US010438835B2

(12) United States Patent
Motz

(10) Patent No.: US 10,438,835 B2
(45) Date of Patent: Oct. 8, 2019

(54) SYSTEM REFERENCE WITH COMPENSATION OF ELECTRICAL AND MECHANICAL STRESS AND LIFE-TIME DRIFT EFFECTS

(71) Applicant: Infineon Technologies AG, Neubiberg (DE)

(72) Inventor: Mario Motz, Wernberg (AT)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 16/127,713

(22) Filed: Sep. 11, 2018

(65) Prior Publication Data
US 2019/0013233 A1    Jan. 10, 2019

Related U.S. Application Data

(62) Division of application No. 14/623,258, filed on Feb. 16, 2015, now Pat. No. 10,103,050.

(51) Int. Cl.
*H01L 21/71*    (2006.01)
*G05D 15/01*    (2006.01)
(Continued)

(52) U.S. Cl.
CPC ............. *H01L 21/71* (2013.01); *G05D 15/01* (2013.01); *G05F 1/56* (2013.01); *G05F 3/02* (2013.01);
(Continued)

(58) Field of Classification Search
CPC ............... G01R 27/02; G01R 27/2611; H01M 2008/1095; H01M 8/04649; G01N 22/00
(Continued)

(56) References Cited

U.S. PATENT DOCUMENTS 3,527,691 A * 9/1970 Hodgson ................. C10G 1/083
208/419
6,005,389 A * 12/1999 Prammer ............. G01N 24/081
324/300
(Continued)

FOREIGN PATENT DOCUMENTS

DE    102005029464 A1    12/2006

OTHER PUBLICATIONS

Ausserlechner, Udo, Mario Motz, and Michael Holliber. "Compensation of the piezo-Hall effect in integrated Hall sensors on (100)-Si." IEEE Sensors journal 7.11 (2007): 1475-1482. (Year: 2007).*
(Continued)

*Primary Examiner* — Christopher P McAndrew
(74) *Attorney, Agent, or Firm* — Eschweiler & Potashnik, LLC

(57) ABSTRACT

Stress compensated systems and methods of compensating for electrical and mechanical stress are discussed. One example system can include a first circuit and a global stress compensation component. The first circuit can be configured to generate a first signal and can comprise at least one local stress compensation component (e.g., employing dynamic element matching, chopping, etc.). The global stress compensation component can comprise one or more stress sensors configured to sense one or more stress components associated with the system. The global stress compensation component can be configured to receive the first signal and to compensate for stress effects on the first signal.

11 Claims, 19 Drawing Sheets

(51) Int. Cl.
*G05F 3/02* (2006.01)
*G01R 27/02* (2006.01)
*G01N 22/00* (2006.01)
*G01R 31/28* (2006.01)
*H01L 23/00* (2006.01)
*H01M 8/04537* (2016.01)
*G05F 1/56* (2006.01)

(52) U.S. Cl.
CPC ............. *G01N 22/00* (2013.01); *G01R 27/02* (2013.01); *G01R 31/2872* (2013.01); *G01R 31/2896* (2013.01); *H01L 23/562* (2013.01); *H01M 8/04649* (2013.01)

(58) Field of Classification Search
USPC ........................................................ 324/602
See application file for complete search history.

(56) References Cited

U.S. PATENT DOCUMENTS

| | | | | |
|---|---|---|---|---|
| 6,392,409 | B1* | 5/2002 | Chen ................... | G01N 24/081 324/303 |
| 6,400,148 | B1* | 6/2002 | Meyer ................... | G01R 33/50 324/300 |
| 7,437,260 | B2* | 10/2008 | Ausserlechner ...... | G01L 5/0047 257/427 |
| 7,440,861 | B2* | 10/2008 | Ausserlechner ...... | G01L 5/0047 323/293 |
| 7,750,743 | B2* | 7/2010 | Ausserlechner ......... | G01D 3/02 327/509 |
| 9,063,198 | B2* | 6/2015 | Okatake ............. | G01R 31/3187 |
| 9,410,820 | B2* | 8/2016 | Ausserlechner ....... | G01D 3/021 |
| 2005/0001487 | A1* | 1/2005 | Ausserlechner ..... | G01D 3/0365 307/100 |
| 2005/0129586 | A1* | 6/2005 | Kao ........................... | B01J 8/22 422/139 |
| 2005/0162160 | A1* | 7/2005 | Ausserlechner ...... | G01L 5/0047 324/251 |
| 2008/0157850 | A1* | 7/2008 | Ausserlechner ........ | G01D 3/02 327/509 |
| 2009/0108839 | A1 | 4/2009 | Ausserlechner | |
| 2010/0018904 | A1* | 1/2010 | Kressmann ............ | C10G 45/18 208/210 |
| 2011/0167713 | A1* | 7/2011 | Quignard .................. | C10G 1/08 44/307 |
| 2011/0193223 | A1* | 8/2011 | Ozaki ...................... | H01L 24/05 257/737 |
| 2011/0209556 | A1 | 9/2011 | Ausserlechner et al. | |
| 2011/0230688 | A1* | 9/2011 | Charon .................. | C10G 1/002 585/240 |
| 2012/0036764 | A1* | 2/2012 | Babe .......................... | C01B 3/04 44/307 |
| 2014/0166540 | A1* | 6/2014 | Guichard ............... | C10G 65/04 208/211 |
| 2014/0340082 | A1* | 11/2014 | Yang .................... | G01N 24/081 324/309 |

OTHER PUBLICATIONS

Makinwa, Kofi AA, et al. "Smart sensor design: The art of compensation and cancellation." Solid State Device Research Conference , 2007. ESSDERC 2007. 37th European. IEEE, 2007. (Year: 2007).*
Fruett, et al. "Minimization of the Mechanical-Stress-Induced Inaccuracy in Bandgap Voltage References." IEEE Journal of Solid-State Circuits, vol. 38, No. 7, Jul. 2003.
Abesingha, et al. "Voltage Shift in Plastic-Packaged Bandgap References." IEEE Transactions on Circuits and Systems—II: Analog and Digital Signal Processing, vol. 49, No. 10, Oct. 2002.
Ausserlechner, Udo, Mario Motz, and Michael Holliber. "Compensation of the piezo-Hall effect in integrated Hall sensors on (100)-Si." IEEE Sensorsjournal7.11 (2007): 1475-1482.
Makinwa, Kofi AA, et al. "Smart sensor design: The art of compensation and cancellation." Solid State Device Research Conference, 2007. ESSDERC 2007. 37th European. IEEE, 2007.
Non-Final Office Action dated Aug. 31, 2017 in connection with U.S. Appl. No. 14/623,258.
Final Office Action dated Nov. 20, 2017 in connection with U.S. Appl. No. 14/623,258.
Notice of Allowance dated Jun. 13, 2018 in connection with U.S. Appl. No. 14/623,258.

* cited by examiner

110

SYSTEM REFERENCE WITH COMPENSATION OF ELECTRICAL AND MECHANICAL STRESS AND LIFE-TIME DRIFT EFFECTS

CROSS REFERENCE TO RELATED APPLICATIONS

This application is a divisional of U.S. application Ser. No. 14/623,258 filed on Feb. 16, 2015, the contents of which are incorporated by reference in their entirety.

FIELD

The present disclosure relates to a system reference that compensates for electrical and mechanical stress, as well as lifetime drift effects.

BACKGROUND

Chips, especially chips in packages, are subject to mechanical stress effects and life-time drift effects that negatively affect performance. As an example, system voltage references, such as bandgap references, are used in a wide variety of systems. However, mechanical stress effects (such as those caused by packaging in plastic)—as well as life-time drift effects—can affect the accuracy of the reference voltage over time, leading to a degradation in system performance.

DETAILED DESCRIPTION

Figure 1:
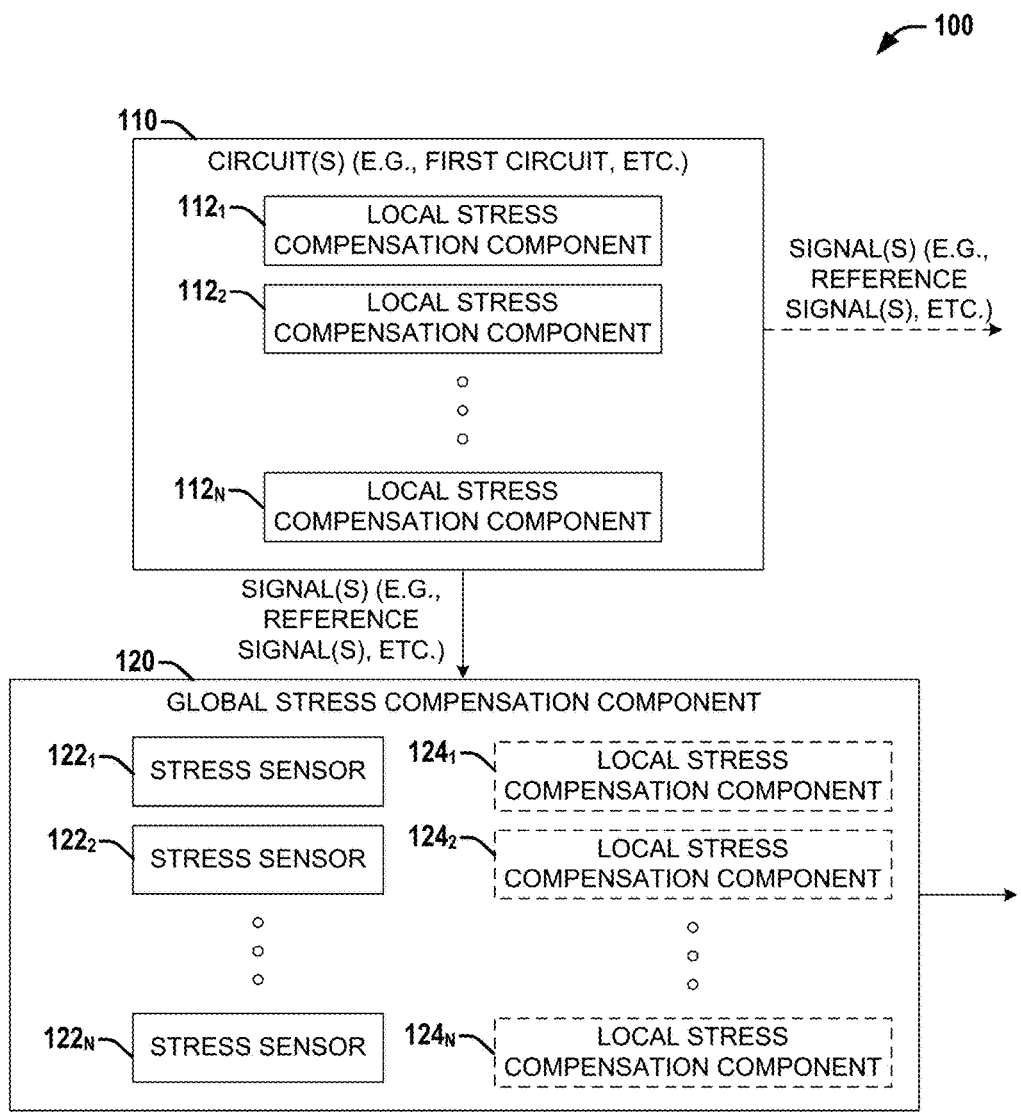
FIG. 1 is a block diagram illustrating an example system that compensates for stress effects on at least one signal according to various aspects described herein.

The present disclosure will now be described with reference to the attached drawing figures, wherein like reference numerals are used to refer to like elements throughout, and wherein the illustrated structures and devices are not necessarily drawn to scale. As utilized herein, terms "component," "system," "interface," and the like are intended to refer to a computer-related entity, hardware, software (e.g., in execution), and/or firmware. For example, a component can be a processor (e.g., a microprocessor, a controller, or other processing device), a process running on a processor, a controller, an object, an executable, a program, a storage device, a computer, a tablet PC and/or a mobile phone with a processing device. By way of illustration, an application running on a server and the server can also be a component. One or more components can reside within a process, and a component can be localized on one computer and/or distributed between two or more computers. A set of elements or a set of other components can be described herein, in which the term "set" can be interpreted as "one or more."

Further, these components can execute from various computer readable storage media having various data structures stored thereon such as with a module, for example. The components can communicate via local and/or remote processes such as in accordance with a signal having one or more data packets (e.g., data from one component interacting with another component in a local system, distributed system, and/or across a network, such as, the Internet, a local area network, a wide area network, or similar network with other systems via the signal).

As another example, a component can be an apparatus with specific functionality provided by mechanical parts operated by electric or electronic circuitry, in which the electric or electronic circuitry can be operated by a software application or a firmware application executed by one or more processors. The one or more processors can be internal or external to the apparatus and can execute at least a part of the software or firmware application. As yet another example, a component can be an apparatus that provides specific functionality through electronic components without mechanical parts; the electronic components can include one or more processors therein to execute software and/or firmware that confer(s), at least in part, the functionality of the electronic components.

Use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. Furthermore, to the extent that the terms "including," "includes," "having," "has," "with," or variants thereof are used in either the detailed description and the claims, such terms are intended to be inclusive in a manner similar to the term "comprising."

Embodiments discussed herein can achieve very high accuracy signals (e.g., reference voltages, currents, and/or clock signals, etc.) for systems on chips or systems in packages, compensating for stress effects over the lifetime of the system and through temperature cycling.

Referring to FIG. 1, illustrated is a block diagram of an example system 100 that compensates for stress effects on at least one signal according to various aspects described herein. As used herein, stress effects include the effects of mechanical stress (including piezoresistive and piezojunction effects, the effects of temperature cycling or temperature gradients, humidity changes) and electrical stress (including changes in parameters of transistors and other components, such as those caused by applied supply voltages). System 100 includes one or more circuits 110 (e.g., a first circuit, second circuit, etc.) that can each include a first set of one or more local stress compensation components $112_1$-$112_N$, and a global stress compensation component 120 that includes one or more stress sensors $122_1$-$122_N$ and optionally includes a second set of one or more local stress compensation components $124_1$-$124_N$. In various aspects, system 100 can be included as part of a system on chip or system in package to compensate for stress effects, including in a multi-chip package with a chip-on-chip arrangement, where stress effects are particularly high.

Although, in general, system 100 can include more than one circuit 110, for ease of discussion, the following is described in connection with a first circuit 110, with similar details applicable to any additional circuits 110 included in system 100. First circuit 110 is configured to generate the at least one signal (e.g., a first signal, a second signal, etc.). Although, solely for purposes of illustration, examples and discussions are provided herein wherein first circuit 110 comprises a reference circuit (e.g., bandgap reference, etc.), the systems, components, and techniques described herein can be applied to embodiments wherein first circuit 110 comprises any circuit that generates at least one output signal (e.g., temperature sensor, etc.). In embodiments wherein first circuit 110 comprises a reference circuit, the at least one signal can comprise at least one reference signal (e.g., one or more reference voltages, one or more reference currents, one or more reference clock frequencies, etc.). The first circuit 110 outputs the at least one signal to the global stress compensation component 120, and depending on the embodiment, may also be output to one or more other components, such as a system ADC or a system amplifier. Depending on the specific embodiment, the first circuit 110 can include a variety of components for generating the at least one signal. For example, the first circuit can comprise a bandgap reference or some other system reference (e.g., analog-to-digital converter (ADC), etc.), and can include components to generate the at least one reference signal (e.g., reference voltage(s), reference current(s), reference clock signal(s), etc.), the nature of which vary depending on the specific embodiment. Example embodiments and components that may be included are discussed infra.

The first circuit 110 additionally includes a first set of one or more local stress compensation components $112_1$-$112_N$ that compensate for stress effects (e.g., local stress effects within the first circuit 110, such as mechanical stress effects, electrical stress effects, aging effects, etc., for example, mechanical stress effects caused by proximity to trenches, etc.) on the at least one signal (e.g., at least one reference signal, etc.). For example, the first set of one or more local stress compensation components $112_1$-$112_N$ can include choppers that chop input and/or output signals of one or more components (e.g., amplifier(s), ADC(s), etc.) of the first circuit 110, which can compensate for local stress effects (e.g., by reducing drift). As another example, the first set of one or more local stress compensation components $112_1$-$112_N$ can include one or more dynamic element matching (DEM) components to employ DEM to cycle between a plurality of components (e.g., transistors, resistors, etc.) of the first circuit 110 (or components thereof, such as transistors of a current mirror of the first circuit 110, etc.), thereby reducing local stress effects associated with individual components by averaging out their random local stress effects. In a further example, the first set of one or more local stress compensation components $112_1$-$112_N$ can include one or more auto-zeroing components (e.g., an auto-zero amplifier, etc.) to compensate for local stress effects by reducing drift. Chopping and auto-zeroing are two techniques or arrangements of elements that can each compensate for offset effects. Auto-zeroing has the same effect of canceling an offset (e.g., of an amplifier, an ADC, etc.) as chopping. However, instead of exchanging the inputs in different phases of a cycle (as in chopping), in auto-zeroing a first phase is used to shortcut the input to store the offset, and a second phase is used to connect the component (amplifier, etc.) to a sensor or input signal and subtract the previously measured offset signal. Discussion herein (and illustration in the figures) of choppers, chopped signals, chopping, etc. is also intended to include, additionally or alternatively, aspects where a similar effect is accomplished via auto-zeroing components, auto-zeroed signals, auto-zeroing, etc.

The global stress compensation component 120 can also compensate for stress effects (e.g., global stress effects affecting the system 100, etc.) on the at least one signal, and can include one or more components (which depend on the embodiment) to compensate for stress effects on the at least one signal in various ways (e.g., by receiving the at least one signal and outputting at least one compensated signal, by generating at least one compensation signal or output that can be combined (e.g., additively, multiplicatively, etc) with the at least one signal, etc.). The global stress compensation component 120 can include one or more stress sensors $122_1$-$122_N$ that can sense one or more stress components (e.g., components of a stress tensor, or functions thereof, such as linear combinations) associated with the system 100. Based at least in part on the sensed stress component(s), the global stress compensation component 120 can compensate for the stress effects on the at least one signal. After local and global stress compensation, the final compensated at least one signal (e.g., reference voltage, current, etc.) is independent of physical and other characteristics such as temperature, supply voltage, stress, sensor signal(s), etc.

In aspects, the global stress compensation component 120 can include a plurality of stress sensors $122_1$-$122_N$, and at least two of the plurality of stress components can sense distinct stress components, for example, two or more of a first stress component (e.g., $\sigma_{xx}$), a second stress component orthogonal to the first (e.g., $\sigma_{yy}$), a sum of two orthogonal stress components ($\sigma_{xx}+\sigma_{yy}$), a difference of two orthogonal stress components ($\sigma_{xx}-\sigma_{yy}$), etc.

In aspects, global stress compensation component 120 can include the second set of local stress compensation components $124_1$-$124_N$, which can compensate for stress effects in the global stress compensation component 120 which might otherwise affect the ability of global stress compensation component 120 to compensate for stress effects on the at least one signal. The second set of local stress compensation components $124_1$-$124_N$ can include one or more components similar to those described in connection with the first set of local stress components $112_1$-$112_N$, such as DEM components, choppers (e.g., of amplifiers and/or ADCs, etc.), auto-zeroing components, etc. For example, the global stress compensation component 120 can include a plurality of stress sensors $122_1$-$122_N$ and the second set of local stress compensation components $124_1$-$124_N$ can include a DEM component to cycle between some or all of the plurality of stress sensors $122_1$-$122_N$. In further aspects, DEM can be combined with a plurality of sensors $122_1$-$122_N$ that sense distinct stress components, such that for each distinct stress component (or a subset thereof), a plurality of sensors that sense that distinct stress component can be cycled between via a DEM component. In another example, the second set of one or more local stress compensation components $124_1$-$124_N$ can include choppers that chop input and/or output signals of one or more components (e.g., ADC(s), etc.) of global stress compensation component 120.

Although in some aspects the compensated at least one signal can be represented in an analog manner, in other aspects, the compensated at least one signal can be represented digitally. For example, consider an ADC reference has moderate stress dependence, such as the following reference voltages at different stresses: 1V at 0 MPa, 1.002 V at 100 MPa, and 1.004 V at 200 MPa (e.g., 2%/GPa). With a stable input voltage at the ADC, the digital ADC output would decay slightly as follows: by 1/1.000 at 0 MPa, by 1/1.002 at 100 MPa, and by 1/1.004 at 200 MPa. In such a situation, digital correction after the ADC can compensate to eliminate the effects of stress by multiplying the output as follows: by 1.000 at 0 MPa, by 1.002 at 100 MPa, and by 1.004 at 200 MPa. In such a way, the digital system reference can be stabilized.

Figure 2:
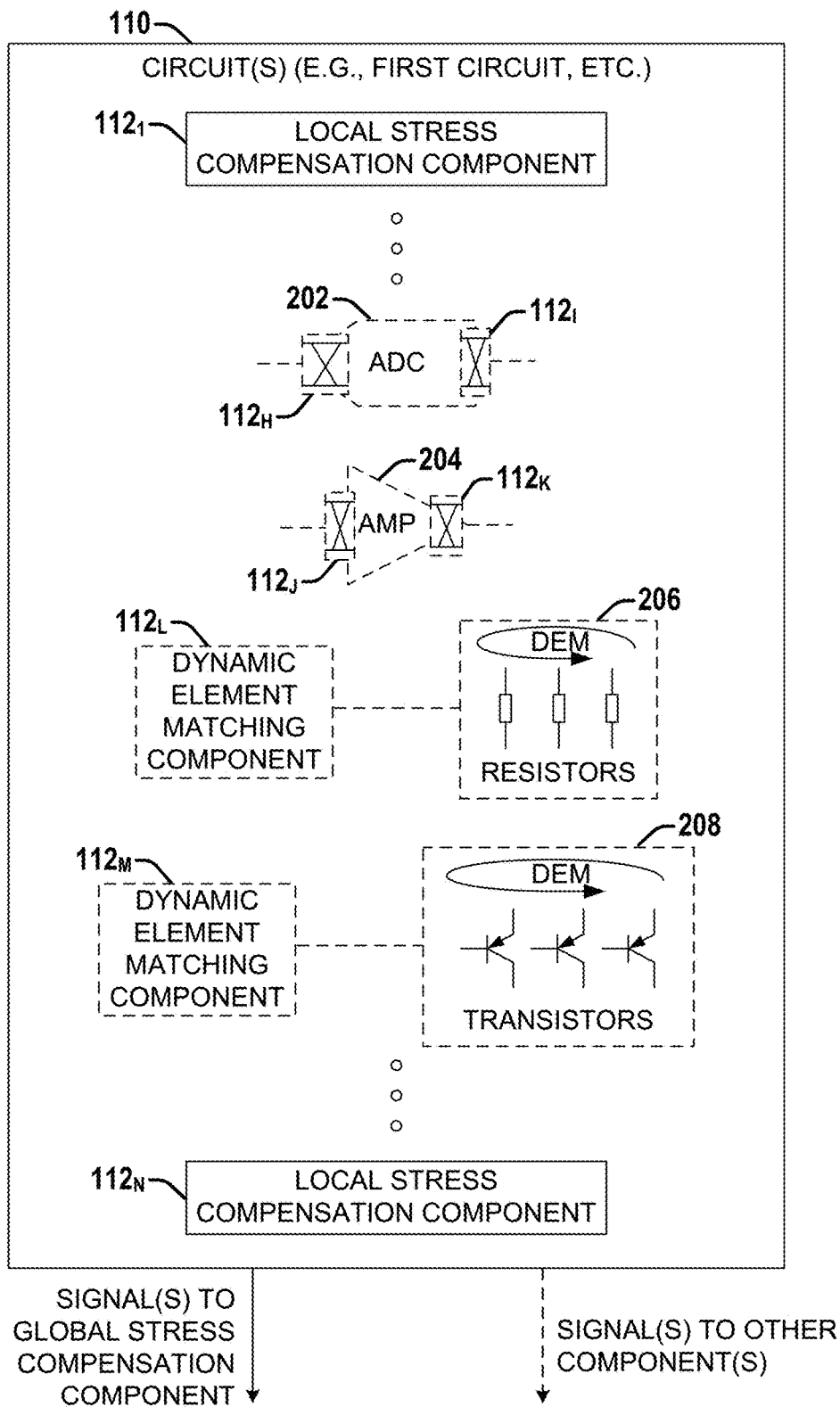
FIG. 2 is a block diagram illustrating an example first circuit, showing example local stress compensation components that can compensate for local stress effects on at least one signal output by the first circuit according to various aspects described herein.

FIG. 2 illustrates a block diagram of an example first circuit 110, showing example local stress compensation components $112_1$-$112_N$ that can compensate for local stress effects on the at least one signal according to various aspects described herein. In embodiments in which the first circuit 110 comprises an ADC 202, the first set of local stress components $112_1$-$112_N$ can optionally include an ADC input chopper $112_H$ (e.g., an analog chopper) to chop an input signal of the ADC and/or an ADC output chopper $112_I$ (e.g., a digital chopper) to chop an output signal of the ADC. In embodiments in which the first circuit 110 comprises an amplifier 204, the first set of local stress components $112_1$-$112_N$ can optionally include an amplifier input chopper $112_J$ (e.g., an analog chopper) to chop an input signal of the amplifier and/or an amplifier output chopper $112_K$ (e.g., a digital chopper) to chop an output signal of the amplifier. Additionally, the first set of local stress compensation components $112_1$-$112_N$ can include at least one dynamic element matching component $112_L$ to cycle between (e.g., rotationally exchange, etc.) a plurality of resistors 206 of the first circuit 110, and/or at least one dynamic element matching component $112_M$ to cycle between a plurality of transistors 208 (e.g., of a current mirror, transistors outputting a reference voltage, etc.) of the first circuit 110.

Figure 3:
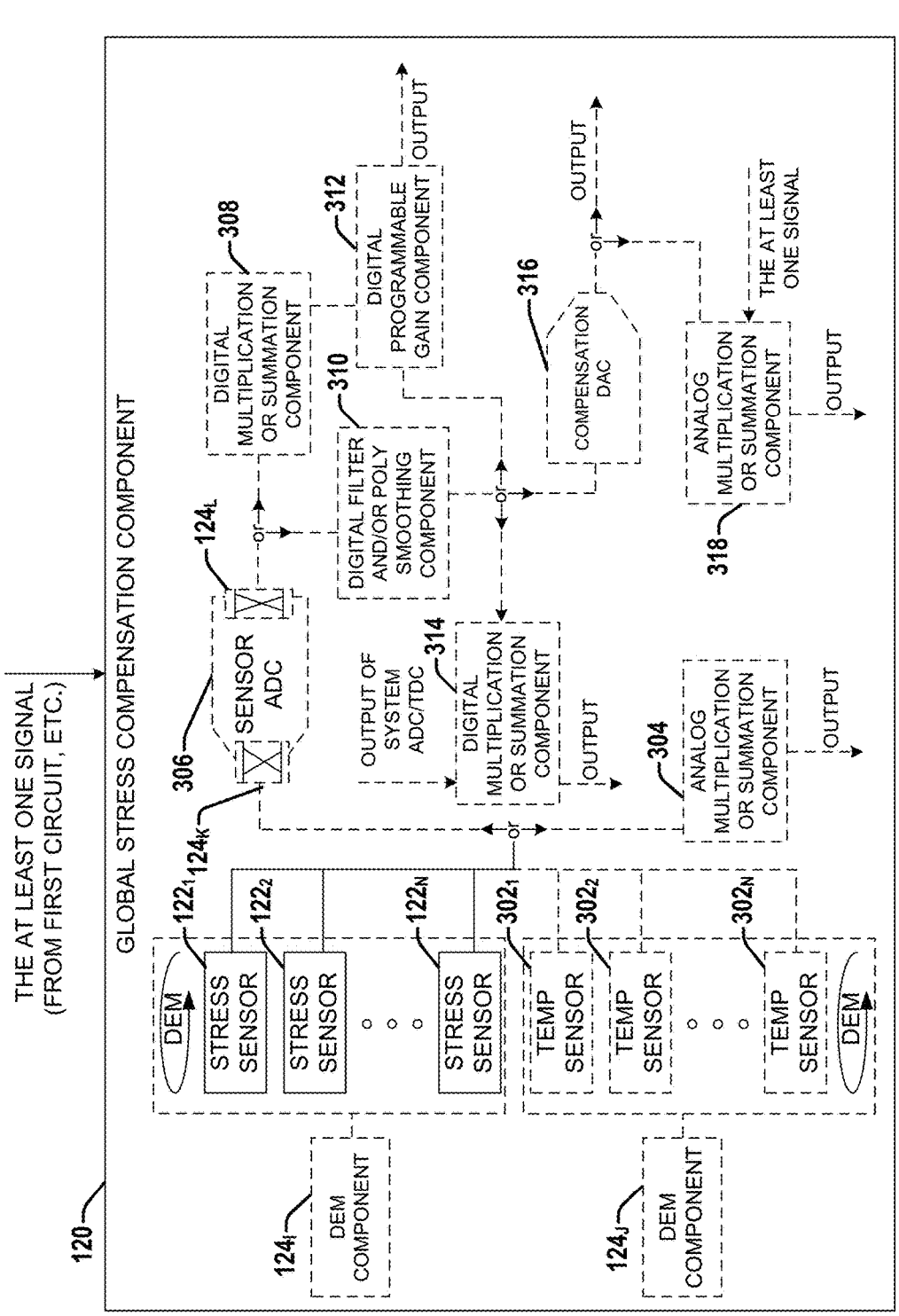
FIG. 3 is a block diagram illustrating multiple variations of an example global stress compensation component showing optional local stress compensation components and other components that can be included in the global stress compensation component, according to various aspects described herein.

FIG. 3 illustrates a block diagram showing multiple variations of an example global stress compensation component 120, showing optional local stress compensation components $124_1$-$124_N$ and other components that can be included in the global stress compensation component, according to various aspects described herein. In aspects, at least one DEM component $124_I$ can be included to employ DEM to cycle between one or more stress sensors $122_1$-$122_N$. Additionally, one or more temperature sensors $302_1$-$302_N$ can be included to measure one or more temperatures and/or temperature gradients associated with a system (e.g., system 100). In aspects, a quadratic or other higher order temperature compensation circuit or curvature temperature compensation circuit can be included to compensate for the effects of the one or more temperatures and/or temperature gradients on the at least one signal. Optionally, at least one DEM component $124_J$ can be included to employ DEM to cycle between the one or more temperature sensors $302_1$-$302_N$. In aspects, chopping can also be employed in connection with the stress sensors and/or temperature sensors.

Figure 4:
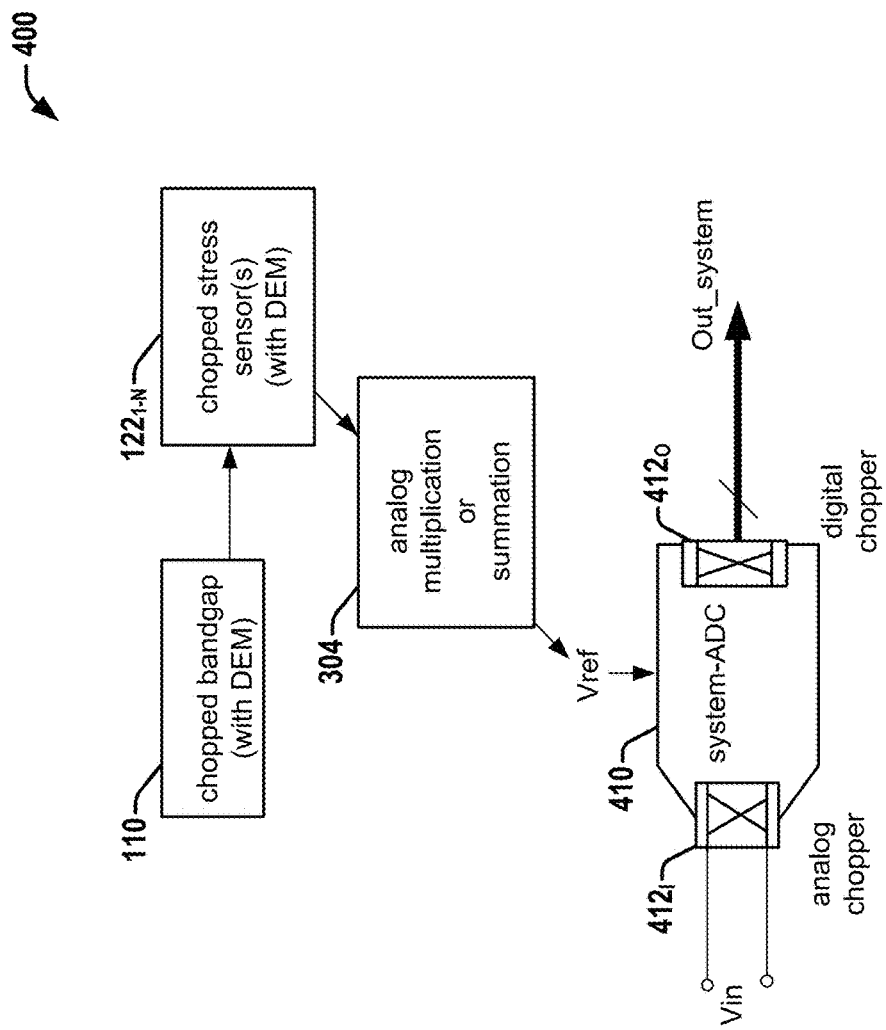
FIG. 4 is a block diagram illustrating an example system that can generate at least one compensated signal via analog multiplication or summation according to various aspects described herein.

In one example embodiment, at least one compensation signal can be generated based on the output(s) of the one or more stress sensors $122_1$-$122_N$ and/or the one or more temperature sensors $302_1$-$302_N$, and the at least one compensation signal can be combined (e.g., via an analog multiplication or summation component 304, etc.) with the at least one signal to compensate for stress effects on the at least one signal (e.g., by generating at least one compensated signal, etc.). FIG. 4 illustrates a block diagram of an example system 400 that can generate at least one compensated signal via analog multiplication or summation (e.g., via an analog multiplier, analog gain adjusting amplifier stages, etc.) according to various aspects described herein. In example system 400, first circuit 110 is a chopped bandgap reference that employs DEM and outputs at least bandgap reference voltage as one of the at least one signals, and the one or more stress sensors $122_1$-$122_N$ are also chopped and employ DEM. The compensated reference voltage can be provided as a stress-compensated reference to a system ADC 410, which can have a chopped input (via analog system ADC input chopper $412_I$) and a chopped output (via analog system ADC output chopper $412_O$) as part of a third set of local stress compensation components to compensate for local stress effects in the at least one component receiving the at least one compensated signal (in this case, system ADC 410).

In other example embodiments, the output of the one or more stress sensors $122_1$-$122_N$ and/or the one or more temperature sensors $302_1$-$302_N$ can be received by a sensor ADC 306, which can generate an output that can be employed in multiple ways to compensate for stress effects on the at least one signal (e.g., by generating at least one compensation signal that can be combined with the at least one signal to compensate for the stress effects, by generating at least one compensated signal that can be employed as compensated replacement(s) for the at least one signal, etc.). Additionally, the second set of local stress compensation components $124_1$-$124_N$ can include at least one of a sensor ADC input chopper $122_K$ (e.g., an analog chopper) or a sensor ADC output chopper $122_L$ (e.g., a digital chopper).

Figure 5:
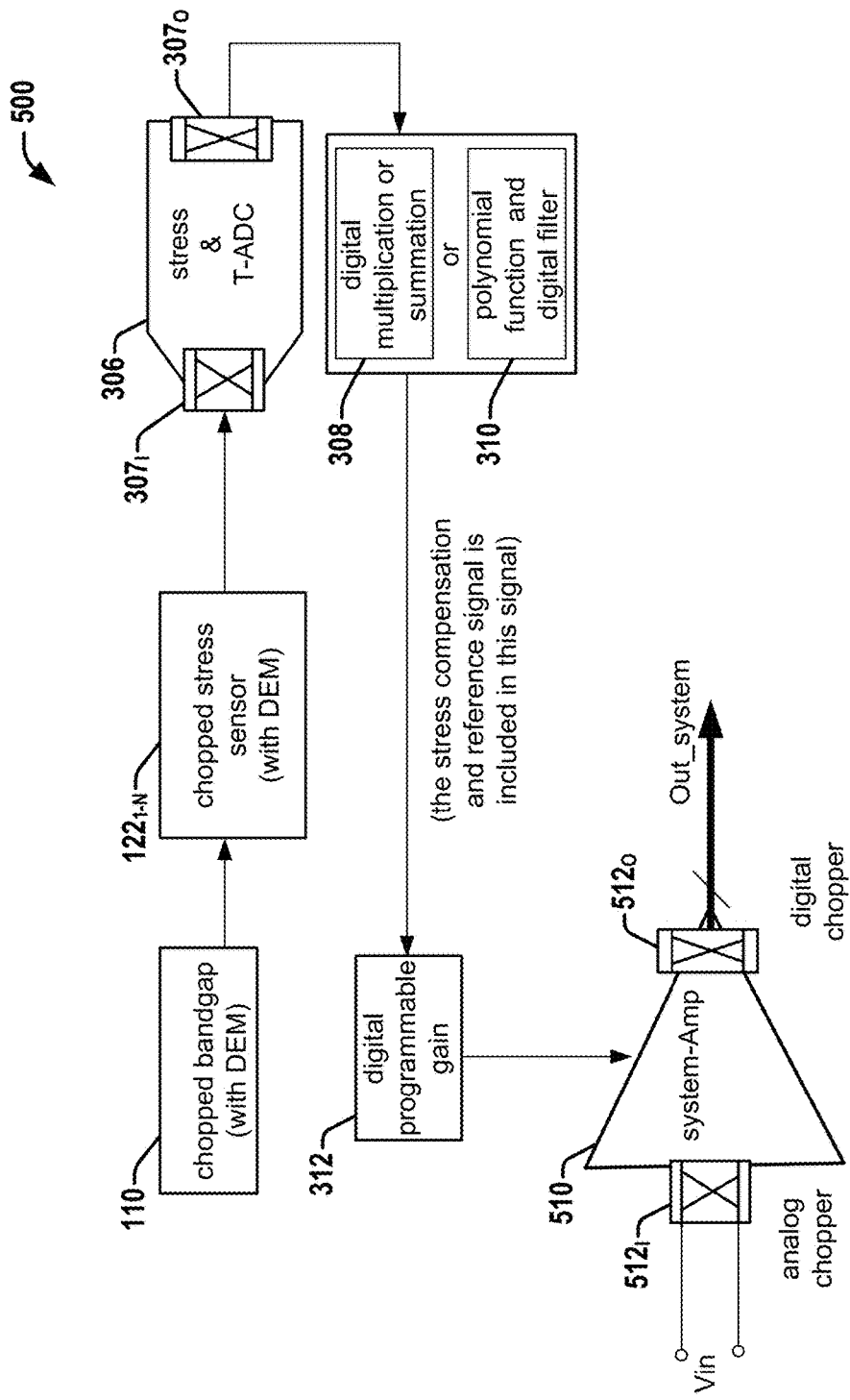
FIG. 5 is a block diagram illustrating an example system that can generate at least one compensated signal via digital multiplication or summation or polynomial smoothing according to various aspects described herein.

In a first set of example embodiments employing sensor ADC 306, the output of sensor ADC 306 can be received by a digital multiplication or summation component 308 or by a digital filter and/or a polynomial smoothing (or compensation) component 310. Whichever of component 308 or component 310 is included can generate at least one compensated signal (e.g., by digital multiplication or summation via component 308, or digital filtering and/or polynomial smoothing via component 310), which can be received by a digital programmable gain component 312 that can set a gain for the at least one compensated signal. FIG. 5 illustrates a block diagram of an example system 500 that can generate at least one compensated signal via digital multiplication or summation or polynomial smoothing according to various aspects described herein. In the example system 500, first circuit 110 is a chopped bandgap reference that employs DEM and outputs at least bandgap reference voltage as one of the at least one signals, and the one or more stress sensors $122_1$-$122_N$ are also chopped and employ DEM. The compensated reference voltage can be provided as a stress-compensated reference to the sensor ADC 306 as described above, and the output signal of digital programmable gain component 312 can be received by a system amplifier 510 as a stress-compensated reference. System amplifier 510 can have a chopped input (via analog system amplifier input chopper $512_I$) and a chopped output (via system amplifier input chopper $412_O$) as part of a third set of local stress compensation components to compensate for local stress effects in the at least one component receiving the at least one compensated signal (in this case, system amplifier 510, with the system reference as the input signal of digital programmable gain component 312).

Figure 6:
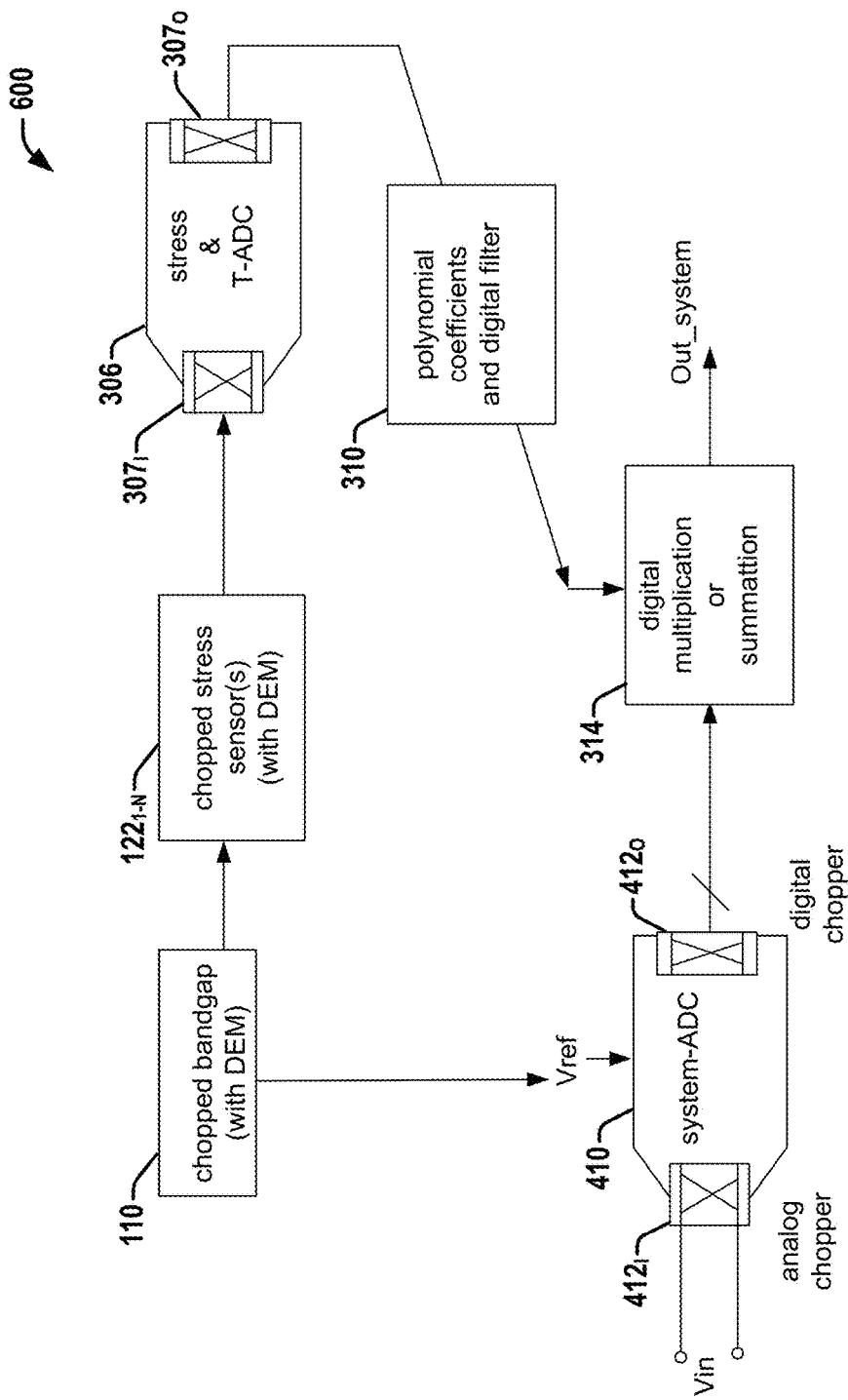
FIG. 6 is a block diagram illustrating an example system that can compensate for stress effects in at least one signal via digital multiplication or summation with at least one compensation signal according to various aspects described herein.

In a next example embodiment employing sensor ADC 306, the output of sensor ADC 306 can be received by the digital filter and/or polynomial smoothing (or compensation) component 310. After digital filtering and/or polynomial smoothing by component 310, at least one compensation signal can be generated which can be provided as output to a digital multiplication or summation component 314. Digital multiplication or summation component 314 can also receive a signal output by a system ADC or a system TDC which received the at least one signal (e.g., reference voltage, etc.) from the first circuit 110, and can digitally sum or multiply the signal output by the system ADC or the system TDC with the at least one compensation signal to compensate for the stress effects on the at least one signal. FIG. 6 illustrates a block diagram of an example system 600 that can compensate for stress effects in at least one signal via digital multiplication or summation with at least one compensation signal according to various aspects described herein. In the example system 600, first circuit 110 is a chopped bandgap reference that employs DEM and outputs at least bandgap reference voltage as one of the at least one signals, and the one or more stress sensors $122_1$-$122_N$ are also chopped and employ DEM. The compensated reference voltage can be provided to the sensor ADC 306 as described above, and can then be provided to a polynomial coefficient and/or digital filter component 310, to generate at least one compensation signal. The reference voltage can also be provided to a system ADC 410, which can have a chopped input (via analog system ADC input chopper $412_I$) and a chopped output (via analog system ADC output chopper $412_O$) as part of a third set of local stress compensation components to compensate for local stress effects in the at least one component receiving the at least one signal (in this case, system ADC 410). The output of the system ADC 410 and the at least one compensation signal from polynomial coefficient and/or digital filter component 310 can be provided to a digital multiplication or summation component 314, which can generate an output signal, thereby compensating for stress effects on the reference voltage.

Figure 7:
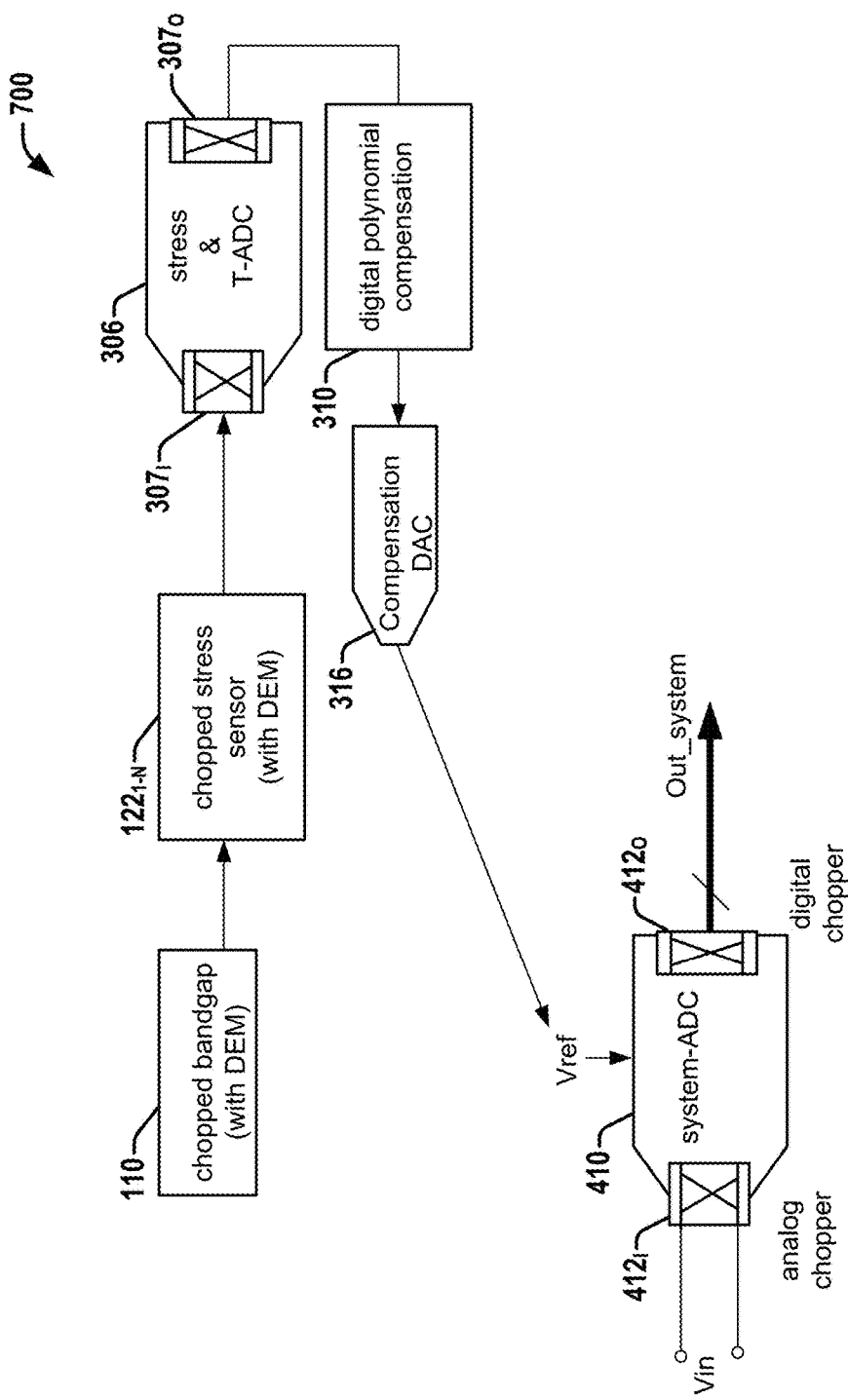
FIG. 7 is a block diagram illustrating an example system that can compensate for stress effects in at least one signal via at least one compensation signal generated by a compensation digital-to-analog converter (DAC) according to various aspects described herein.

In an additional example embodiment employing sensor ADC 306 and the digital filter and/or polynomial smoothing (or compensation) component 310, the output of component 310 can be provided to a compensation digital-to-analog (DAC) converter 316. Compensation DAC 316 can output at least one compensated signal (e.g., compensated reference voltage, etc.). FIG. 7 illustrates a block diagram of an example system 700 that can compensate for stress effects in at least one signal via at least one compensation signal generated by a compensation DAC 316 according to various aspects described herein. In the example system 700, first circuit 110 is a chopped bandgap reference that employs DEM and outputs at least bandgap reference voltage as one of the at least one signals, and the one or more stress sensors $122_1$-$122_N$ are also chopped and employ DEM. The compensated reference voltage can be provided to the sensor ADC 306 as described above, and can then be provided to a digital polynomial compensation component 310. The output of digital polynomial compensation component 310 can be received by compensation DAC 316, which can provide a compensated reference voltage (or reference current, reference resistance, reference capacitance, etc.) to a system ADC 410. System ADC 410 can have a chopped input (via analog system ADC input chopper $412_I$) and a chopped output (via analog system ADC output chopper $412_O$) as part of a third set of local stress compensation components to compensate for local stress effects in the at least one component receiving the at least one signal (in this case, system ADC 410).

Figure 8:
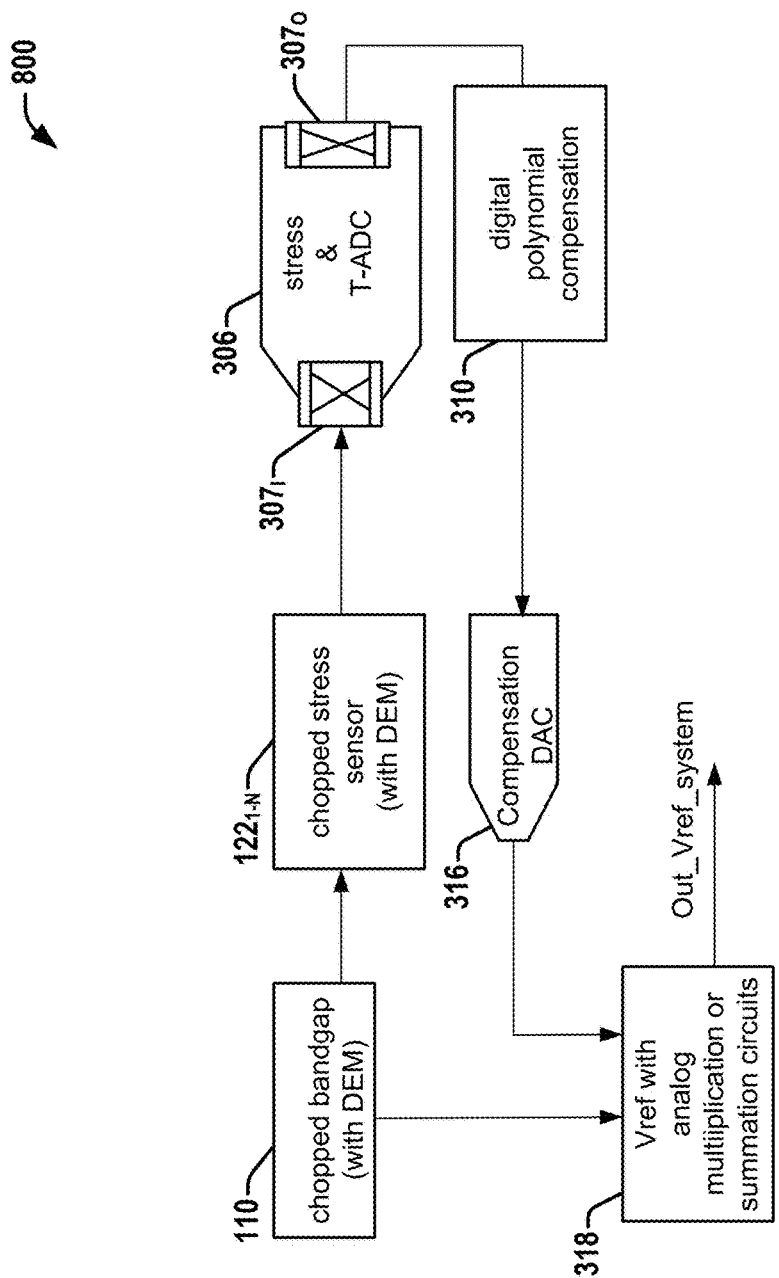
FIG. 8 is a block diagram illustrating an example system that can compensate for stress effects in at least one signal via generating at least one compensated signal via analog summation or multiplication with at least one compensation signal according to various aspects described herein.

A further example embodiment is also described herein employing sensor ADC 306, the digital filter and/or polynomial smoothing (or compensation) component 310, and the compensation DAC 316. In this further example embodiment, the output of compensation DAC 316 (the at least one compensation signal) can be provided to an analog multiplication or summation component 318. Analog multiplication or summation component can multiply or sum the at least one compensation signal with the at least one signal, and output at least one compensated signal. FIG. 8 illustrates a block diagram of an example system 800 that can compensate for stress effects in at least one signal via generating at least one compensated signal via analog summation or multiplication with at least one compensation signal according to various aspects described herein. In the example system 700, first circuit 110 is a chopped bandgap reference that employs DEM and outputs at least bandgap reference voltage as one of the at least one signals, and the one or more stress sensors $122_1$-$122_N$ are also chopped and employ DEM. The compensated reference voltage can be provided to the sensor ADC 306 as described above, and can then be provided to a digital polynomial compensation component 310. The output of digital polynomial compensation component 310 can be received by compensation DAC 316, which can output a compensation signal. The compensation signal and the reference voltage can be received by an analog multiplication or summation component 318, which can output a compensated reference voltage. Alternatively, compensation DAC 316 can be included within analog multiplication or summation component 318, and can comprise one or more of programmable resistor(s), programmable switched capacitor(s) or programmable transistor(s) which can be switched in parallel or in series to adjust the output reference voltage of analog multiplication or summation component 318.

Figure 9:
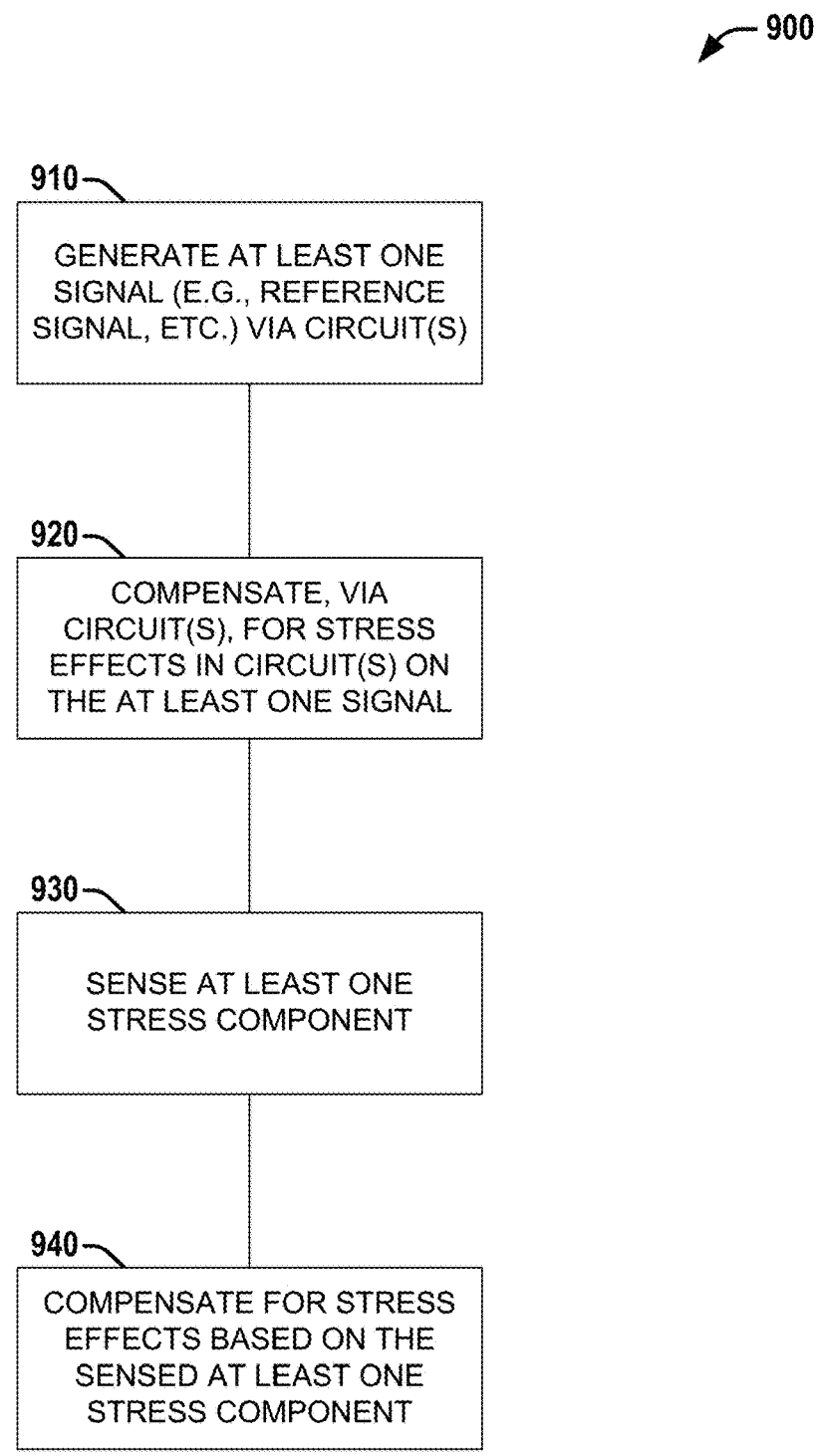
FIG. 9 is a flow diagram illustrating a method of compensating for stress effects in at least one signal according to various aspects described herein.

FIG. 9 illustrates a flow diagram of a method 900 of compensating for stress effects in at least one signal according to various aspects described herein. Method 900 can include, at 910, generating at least one signal (e.g., at least one reference signal, for example, at least one reference voltage, current, or clock frequency) via at least one circuit (e.g., at least one reference circuit). Method 900 can also include, at 920, compensating, via the at least one circuit, for stress effects on the at least one signal (e.g., via chopping, DEM, auto-zeroing, etc.). At 930, method 900 can include sensing at least one stress component (e.g., at least one component of a stress tensor or a function thereof, such as a linear combination of components of the stress tensor). At 940, method 900 can include compensating for the stress effects on the at least one signal based at least in part on the sensed at least one stress component.

Aspects described herein can provide compensation for stress effects in order to provide very high accuracy signals from circuits in a system on chip (including a multi-chip system, e.g., chip-on-chip arrangement, etc.) or a system in package over the lifetime of the system and through temperature cycling. In embodiments with reference circuits (e.g., bandgap references, etc.), on-chip high precision and life-time stable reference voltages or system references can be obtained as described herein, by compensating for aging and other effects caused by electrical and mechanical stress. Such embodiments can provide stable reference signals combined with very low temperature drift and cheap low-power on-chip bandgap references.

Figure 10:
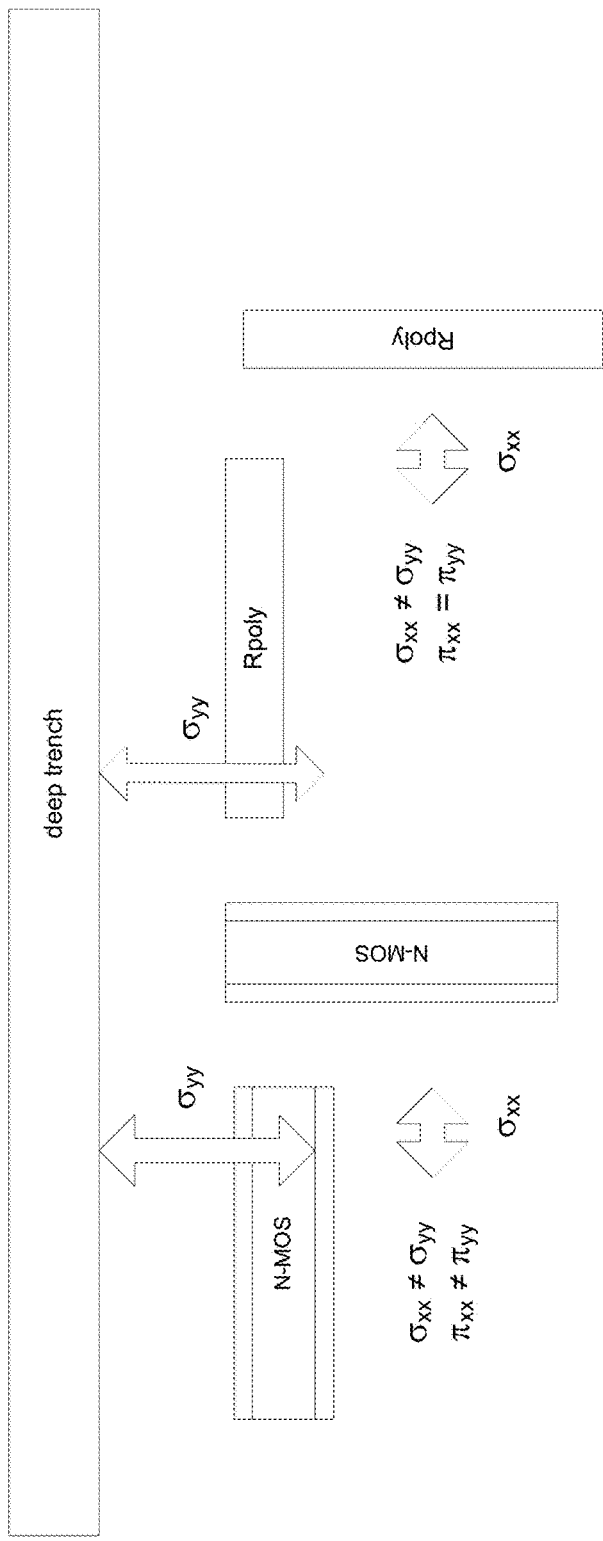
FIG. 10 is a block diagram illustrating different stress components a and piezo coefficients $\pi_{ij}$ that can occur near a trench.

Around 1-7 mV of drift (around 0.1 . . . 0.6% drift) can be caused by the combination of: piezo-junction-effects in bipolar transistors, piezo-resistive effects in resistors, and/or inhomogeneous or direction-dependent stress components in a mounted silicon die, especially with modern technologies using shallow or deep trenches. Additionally, devices in circuits can have different stress dependencies caused by direction or different layout conditions. FIG. 10 illustrates a block diagram showing different stress components $\sigma_{ij}$ and piezo coefficients $\pi_{ij}$ that can occur near a trench. Local variations in $\sigma_{xx}$ and $\sigma_{yy}$ can correlate with global stress variations such as $\sigma_{xx}+\sigma_{yy}$, $\sigma_{xx}-\sigma_{yy}$, or other combinations of stress components.

Figure 11:
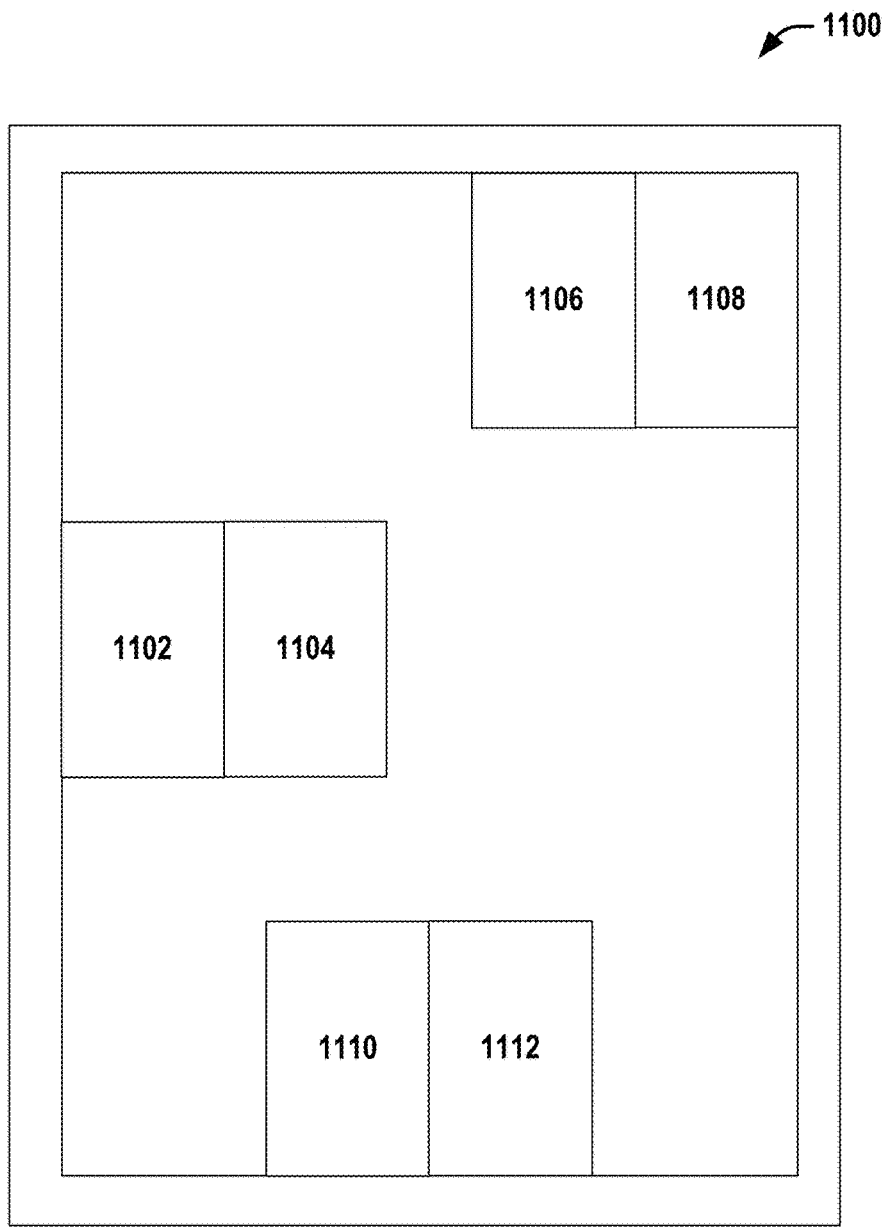
FIG. 11 is a block diagram showing how local stress effects can affect circuits.

Although 50 ppm drift over temperature range has been attempted to be achieved by curvature compensation, lifetime drifts lead to 500 ppm or more over life-time or with humidity changes in plastic packages. One reason for the large drift is mechanical stress caused by one or more of packaging, soldering, humidity changes in plastic packages, bending effects of die, trench influences on neighboring devices, etc. This mechanical stress leads to current and voltage changes in reference circuits and to changes in passive components such as on-chip resistors on the order of 3%, and changes in bipolar transistors in bandgap circuits on the order of 1-7 mV caused by the piezo-junction effects. FIG. 11 illustrates a block diagram showing how local stress effects can affect circuits 1102-1112. Local stress effects are largely unpredictable, but can be caused in part by proximity to trenches, etc., which can significantly impact performance of circuits (e.g., differential input stages, current mirrors, etc.). Circuits 1102 and 1104 are a worst case scenario, wherein only one circuit is in proximity to the trench, causing, in one example measurement, a 13 mV offset difference between the two. Circuits 1106 and 1108 are a better case scenario, wherein both suffer a similar systematic shift, causing, in the example measurement, a 9 mV offset difference between the two. Circuits 1110 and 1112 are a best case scenario, with both experience the same shift, causing, in the example measurement, a 0 mV offset difference between the two.

Figure 12A:
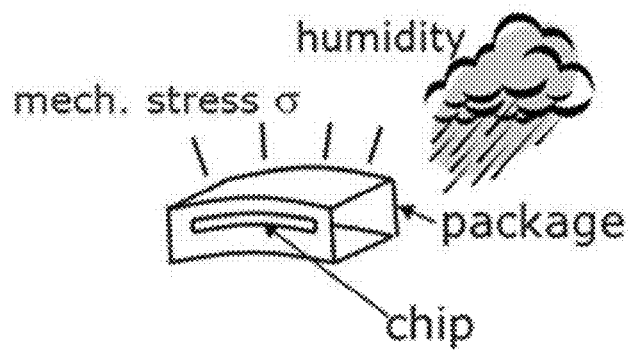
FIG. 12A is a drawing illustrating some potential causes of mechanical stress on a chip.
Figure 12B:
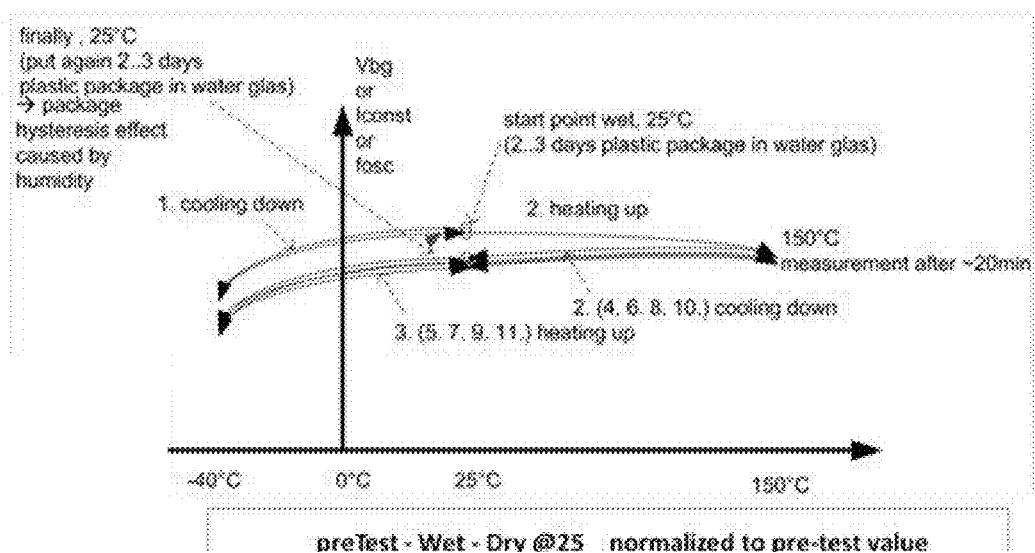
FIG. 12B is a graph illustrating hysteresis effects during temperature cycling caused by mechanical stress changes due to moisture changes in plastic packages.

Although mechanical stress effects are frequently regarded as life-time or temperature cycling effects, approximately up to 90% of mechanical effects can be caused by the combination of packaging, soldering, humidity changes, and temperature gradients on the die. Expansion of the plastic package (e.g., from any of the above-listed causes) can cause bending of the chip, thereby inducing mechanical stress effects. FIG. 12A illustrates a drawing indicating some potential causes of mechanical stress on a chip. FIG. 12B illustrates a graph showing hysteresis effects during temperature cycling caused by mechanical stress changes due to moisture changes in plastic packages.

A second reason for what are commonly considered lifetime or aging effects is that electrical stress changes transistor parameters (for example, during electrical biasing or supplying), causing a mismatch that is unstable and unpredictable, and cannot be compensated fully by mechanical stress sensors. These electrical stress effects can change current mirror ratios and offset voltages of amplifier or differential stages, bandgap current mirrors, current mirrors for stress sensors and offsets of ADCs, etc.

Figure 13:
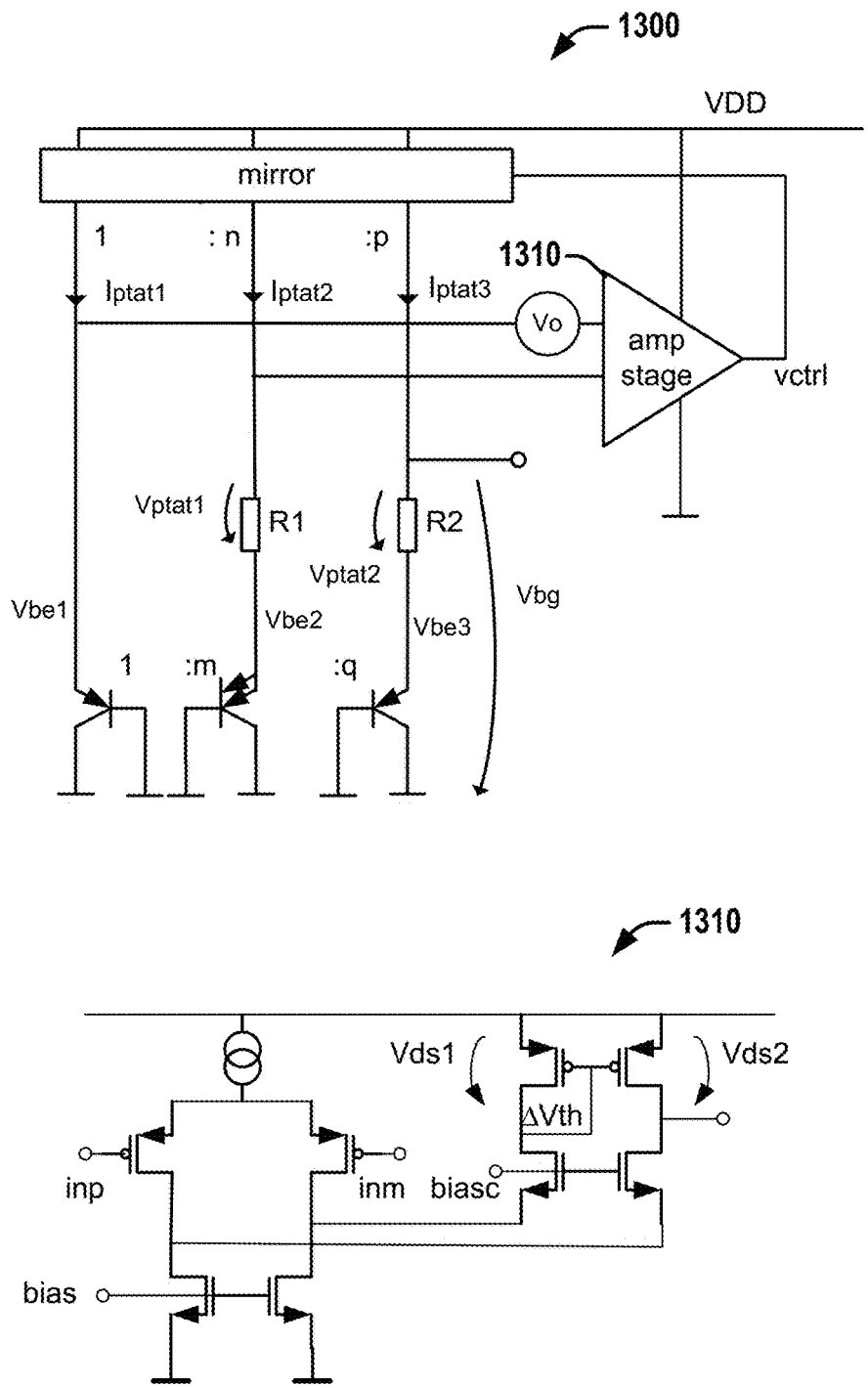
FIG. 13 is a schematic diagram illustrating an example bandgap reference and amplifier stage, showing how electrical stress effects can cause mismatch in various components.

FIG. 13 illustrates a schematic diagram of an example bandgap reference 1300 and amplifier stage 1310, showing how electrical stress effects can cause mismatch in various components. Electrical stress effects over lifetime can lead to changes in any or all of the following, causing mismatch: current mirror ratios (1:n:p in FIG. 13), resistor ratios (R1:R2), Vbe changes (1:m:q), offset changes in the amplifier (e.g., caused by unsymmetrical Vds→ΔVth changes). Statistical measurements have shown a 30% ΔVth drift during lifetime when compared to the original mismatch.

A third problem is flicker noise effects, which changes the bandgap voltage at low frequencies. These effects are also mainly caused by changes in current mirror ratios and offset voltages of the amplifying or differential stage.

Figure 14:
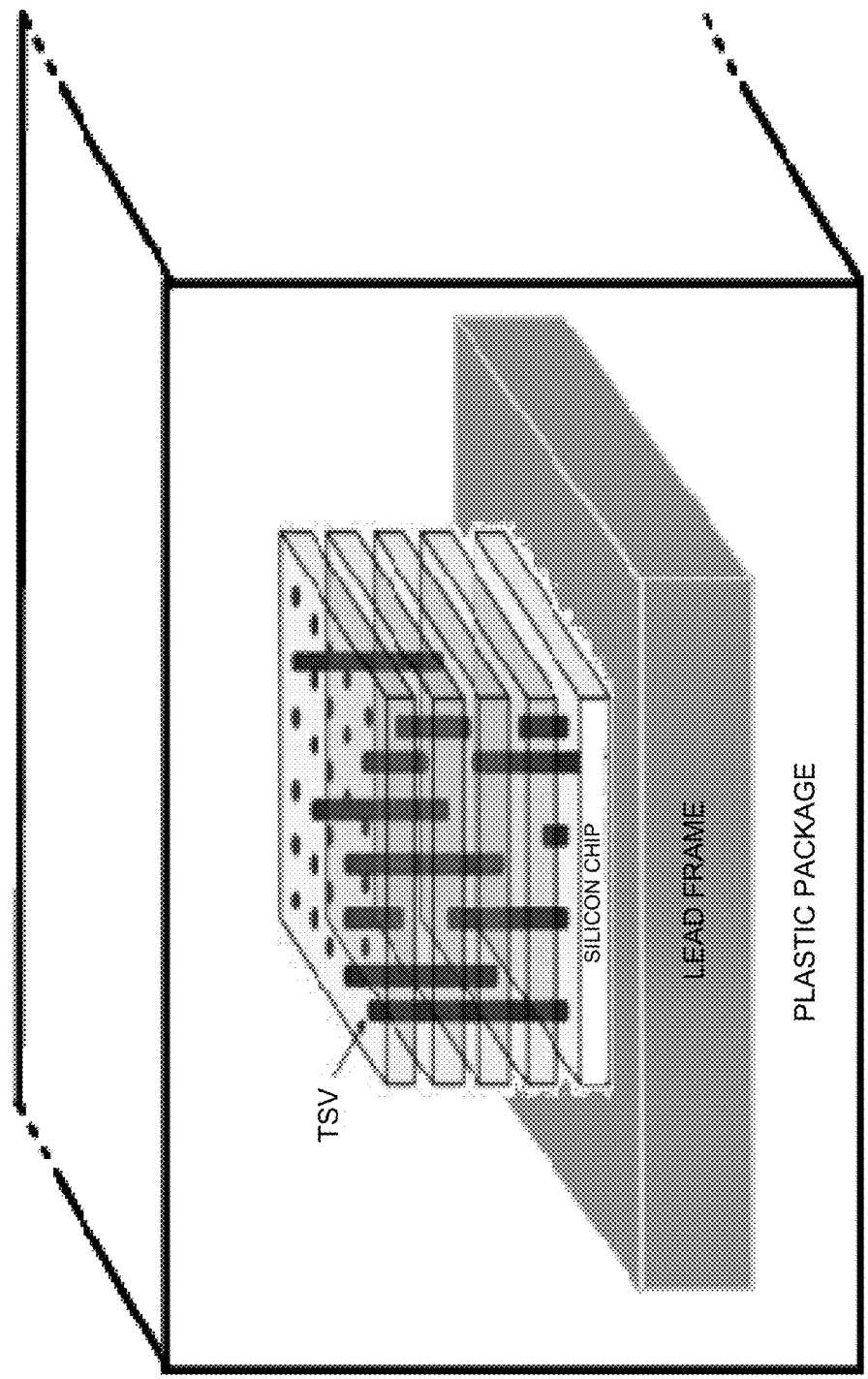
FIG. 14 is a drawing illustrating a multi-chip package with stress effects caused by through-silicon vias (TSVs), different chips, lead frame, and the plastic package each having different thermal expansion coefficients according to various aspects described herein.

A fourth problem is thermal gradients. Usually, thermal gradients can be calibrated for a fixed supply voltage and for a fixed power in the environment of the bandgap. However, supply voltage changes and varying thermal gradients caused by change of power in neighboring circuits can cause additional errors. For example, switching on or off a neighboring microprocessor in a system in chip or system in package can cause thermal gradients that induce additional errors. Variations in thermal expansion coefficients can lead to additional mechanical stress as temperatures or temperature gradients change. FIG. 14 illustrates a drawing of a multi-chip package with stress effects caused by through-silicon vias (TSVs), different chips, lead frame, and the plastic package each having different thermal expansion coefficients.

Any or all of these problems can cause stress effects as the term is used herein.

In the example of a bandgap reference circuit, the bandgap voltage is affected by changes in resistors and their mismatch, bipolar or metal-oxide-semiconductor (MOS) transistors and their mismatches, current mirror mismatches and offset voltage (and offset voltage drift) of amplifier stage(s). The bandgap voltage $V_{BG}$ in a bandgap circuit results from current mirror ratios and the base-emitter voltage $V_{BE}$ of a bipolar transistor, as shown in equations 1 and 2:

$$V_{BG} = V_{BE3} + 2k_c V_T \ln(pm/(nq)) \quad (1)$$

$$V_T = \frac{k_b T}{q_e} \quad (2)$$

where $k_b$ is the Boltzmann constant; $q_e$ is the elementary charge; T is the absolute temperature of the junction; p, q, and n are current mirror ratios, and m is the area ratio.

The base-emitter voltage depends upon the saturation current of the bipolar transistor. In the case of n=p=q=1, then the bandgap voltage is as in equation 3:

$$V_{bg} = (R2/R1)V_T \ln(m) + V_T \ln(V_T \ln(m)) - V_T \ln(R1 I_s). \quad (3)$$

The change in the saturation current due to in-plane stress $\sigma = \sigma_{xx} + \sigma_{yy}$ can be approximated as in equation 4:

$$I_s \approx I_{s0}(T)(1 - \zeta_{12}\sigma) \quad (4)$$

and the change in the bandgap voltage due to changes in in-plane stress $\sigma = \sigma_{xx} + \sigma_{yy}$ is as in equation 5:

$$V_{bg}(\sigma + \Delta\sigma) - V_{bg}(\sigma) = V_T \ln\{[R2(\sigma)/R2(\sigma + \Delta\sigma)] \times [I_s(\sigma)/I_s(\sigma + \Delta\sigma)]\}. \quad (5)$$

The stress dependency of a bandgap voltage is mainly determined by the stress dependency of resistors or current mirrors and the saturation current of bipolar transistor. However, additional stress dependencies result from local mismatches in current mirrors, which are more unpredictable and are subject to electrical lifetime drift effects.

Aspects described herein can compensate for global in-plane stress effects, local mechanical stress effects, and electrical stress effects, to provide more stable and predictable stress compensation coefficients. Thus, signals compensated as described herein have higher and more stable accuracy.

Stress sensors are affected by both temperature and in-plane stress, but with (in general) different stress sensitivities, as shown in equations 6 and 7:

$$R_{lv,n} = R_{lv,n0}(T)(1 + \pi_{lv,n}\sigma) \quad (6)$$

$$R_{v,n} = R_{v,n0}(T)(1 + \pi_{v,n}\sigma). \quad (7)$$

However, the difference of stress components ($\sigma_{xx} - \sigma_{yy}$) can be measured to compensate for systematic local stress effects (e.g., near trenches) or different orientations of transistors and/or resistors in circuits discussed herein (e.g., bandgap references). For example, the stress sensor Vndiff (sensing $\sigma_{xx} - \sigma_{yy}$) shown in FIG. 15 (discussed infra) uses an n-diffusion resistor in an L-shaped arrangement at 45° to the normal chip orientation has a stress dependency of Rlv,n2~1+144%/GPa*($\sigma_{xx} - \sigma_{yy}$).

Embodiments described herein are able to compensate for all mechanical and electrical stress effects on signals. In contrast, conventional systems employing only analog stress compensation (e.g., via combinations of resistors) cannot compensate for all system life-time effects with an ADC reference effect or digital compensation by multiplication or addition of stress dependent compensation values. However, embodiments described herein can provide for electrical life-time drift compensation (e.g., of bandgap circuits, amplifiers in bandgaps, etc.), and can compensate for second or higher order temperature and stress effects. By fully compensating for both electrical and mechanical stress and drift effects, significantly higher overall accuracy can be achieved in system on chip or system in package embodiments. Aspects described herein can provide significant improvements due to a multiplicative effect in achievable accuracy and life-time stability: With better and more accurate stress measurement and initial bandgap reference (e.g., by chopping, DEM, auto-zeroing, etc.), better compensation and more stable stress coefficients can result. In line production, it is not possible to individually find the best correlation coefficients or the best stress coefficients to compensate for the individual variations of each sample. However, aspects described herein can be used to obtain stable coefficients and accurate measurements that can facilitate compensation for at least one design or package.

Figure 15:
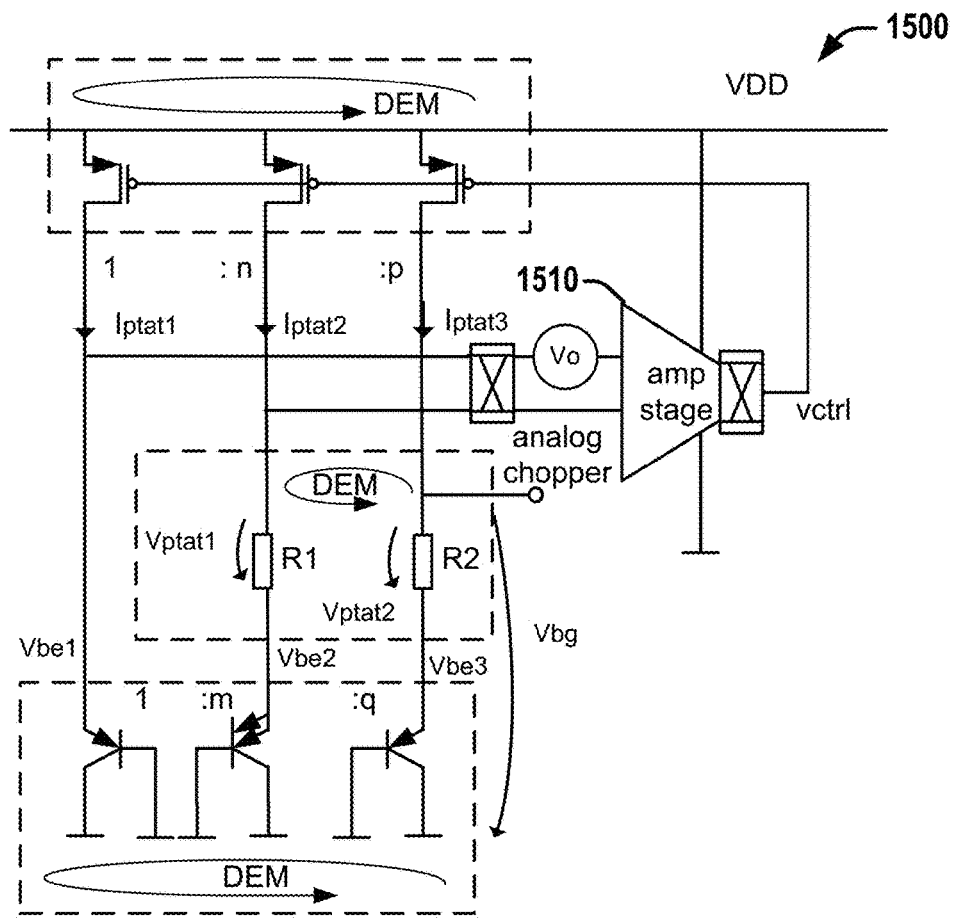
FIG. 15 is a schematic diagram illustrating an example bandgap reference and amplifier stage with DEM and chopping according to various aspects described herein.
Figure 15:
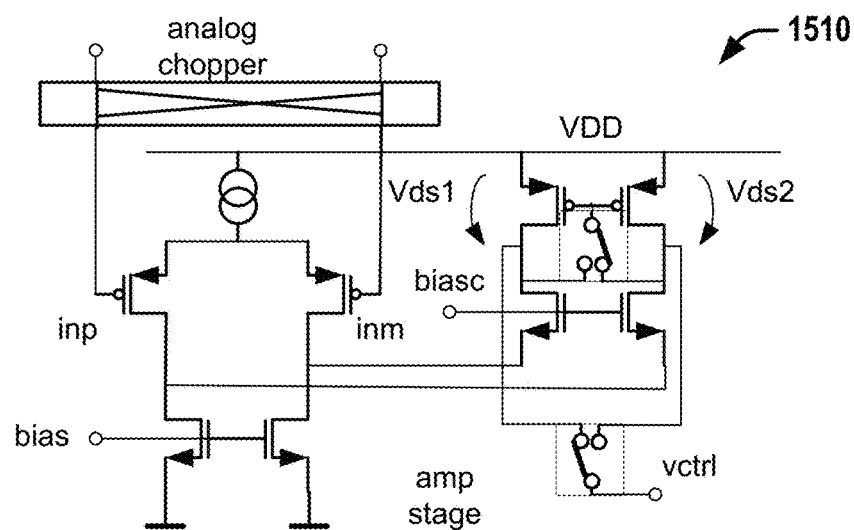
Figure 16:
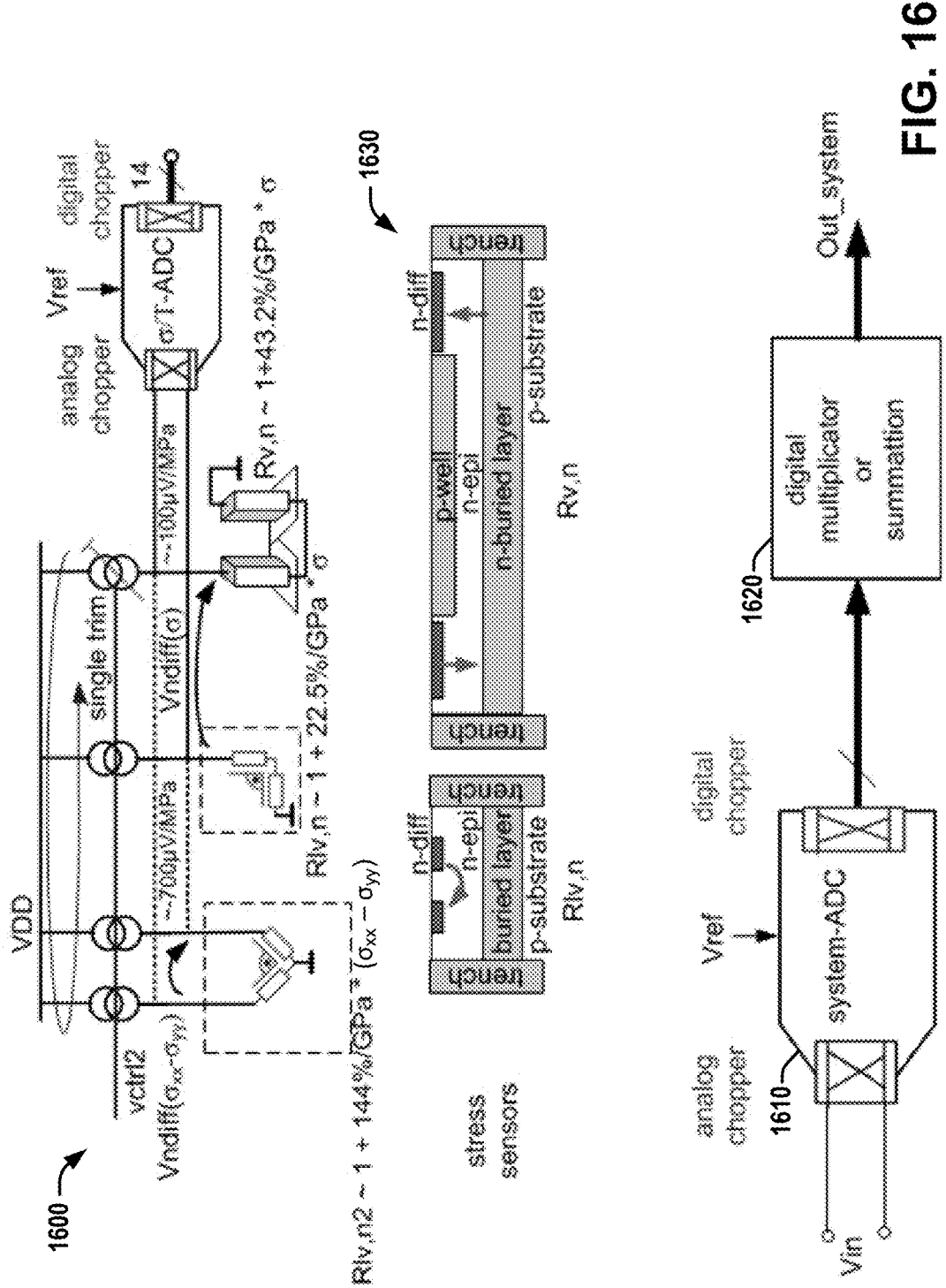
FIG. 16 is a schematic diagram illustrating an example chopped stress sensors with DEM and chopped system ADC according to various aspects described herein.

FIG. 15 illustrates a schematic diagram of an example bandgap reference 1500 and amplifier stage 1510 with DEM and chopping according to various aspects described herein. FIG. 16 illustrates a schematic diagram of an example chopped stress sensors with DEM at 1600 and chopped system ADC at 1610 according to various aspects described herein. The combination of the bandgap reference 1500 and stress sensors 1600 can provided a stress-compensated reference signal for system ADC 1610, such that the system output after digital multiplication or summation at 1620 is compensated for mechanical and electrical stress effects. At 1630, different example configurations of stress sensors are shown, for a lateral stress sensor Rlv,n on the left, and a vertical stress sensor Rv,n on the right. Equations 8 and 9, below, show example weighted bias current generation to compensate for stress effects in circuits:

$$I_{bias\_stresscomp(x+y)} = \frac{V_{replica1\_bandgap}}{(R_{lv,n}(\sigma, T) + k_1 \cdot R_{v,n}(\sigma, T))} \sim \frac{1}{1 + (22.5\%/GPa) + k_1 \cdot (43.2\%/GPa)} \quad (8)$$

$$I_{bias\_stresscomp(x-y)} = \frac{k_2 \cdot V_{replica2\_bandgap}}{(R_{lv,n+45°}(\sigma, T) - R_{vl,n-45°}(\sigma, T))} \sim \frac{k_2}{1 + (144\%/GPa)} \quad (9)$$

where $k_1$ can have positive or negative values.

Figure 17:
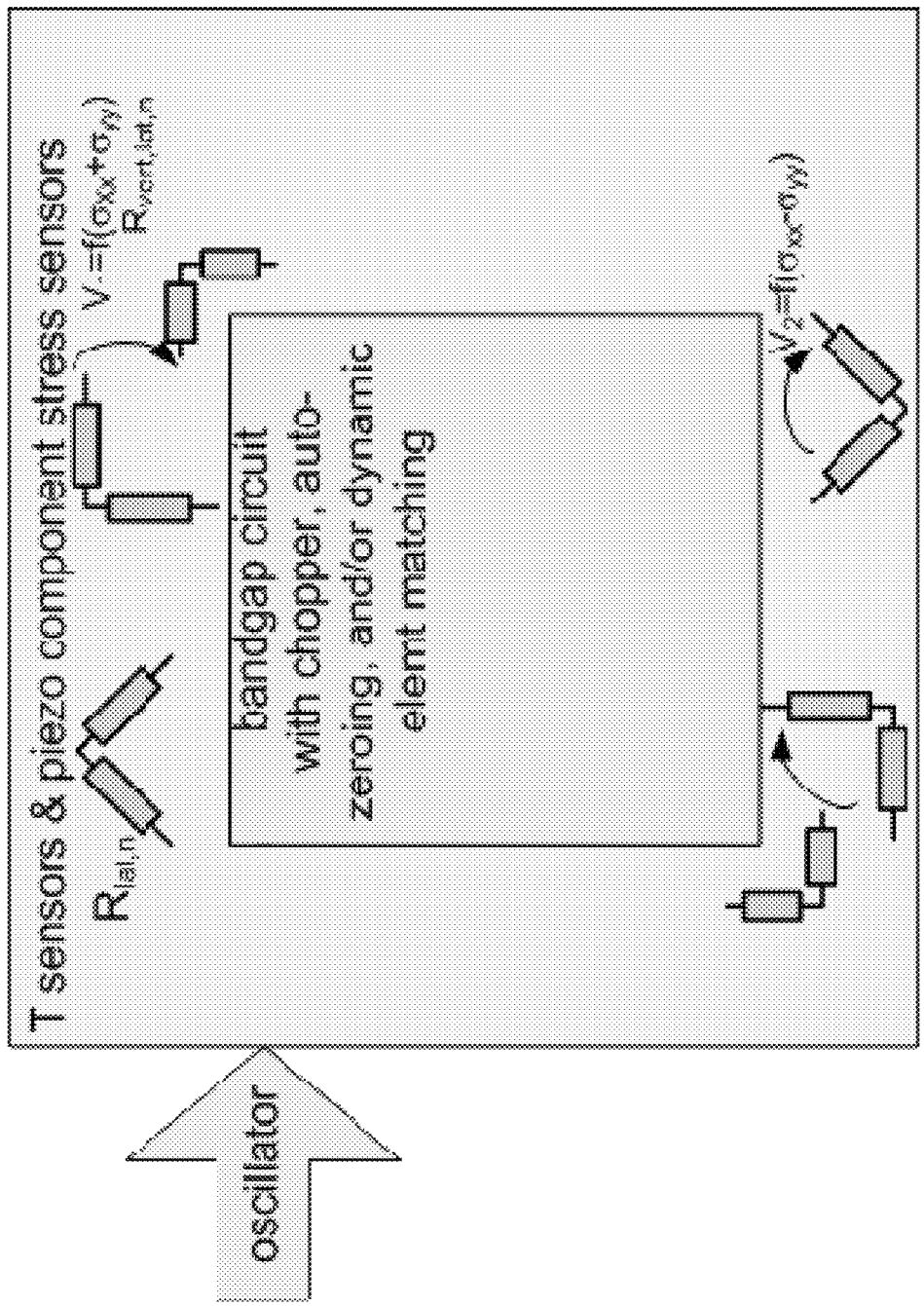
FIG. 17 is a diagram illustrating an example layout of a system including a bandgap circuit and sensors according to various aspects described herein.

FIG. 17 illustrates a diagram of an example layout of a system including a bandgap circuit and sensors according to various aspects described herein. Stress measurement in the example layout shown in FIG. 17 can be accomplished by differential voltage measurement. As seen in the stress sensors around the bandgap circuit of FIG. 17, different mechanical stress coefficients can be used, which can be accomplished by using two different resistor types in the current sources and bandgap-based replica circuits. As an illustrative example, 45° to wafer flat and lateral L-shaped n-diffusion or n-well resistor(s) with a positive piezo-resistive effect of $\pi_{xx} + \pi_{yy} = -24\%/GPa$ (sum) and $\pi_{xx} - \pi_{yy} = +$ 144%/GPa can be used in combination with vertical n-diffusion or n-well resistor(s) with $\pi_{xx}+\pi_{yy}=+52\%$/GPa (sum). By using these different resistors, different (e.g., X and Y) stress dependent correction signals can be derived. These correction signals can be analog voltages or currents, etc., or digital correction signals derived from a stress sensor via an ADC.

The bandgap-based reference voltage Vref is temperature-compensated and has low stress-dependency (due to small piezo-junction effects and small influence of piezo-resistance effect of used resistors). The main source of stress effects is from the bias resistors and bipolar transistors used in the bandgap. Additionally, mismatch effects lead to mechanical and electrical drifts of the bandgap voltage.

Frequently used n-doped poly-resistors have a stress coefficient of −11%/GPa, which causes around a 1-2 mV shift at 200 MPa of in-plane stress in and around the middle of the chip (e.g., caused by a normal packaging process), and around +/−0.01-0.07% instability from humidity changes, lifetime effects, and soldering.

Although near trenches the stress can change in a different manner (e.g., with values having an X or Y dependency), these local stresses still correlate with the global stress. These effects can be compensated with a second constant current, which can also use bandgap-inherent voltages $V_{PTAT}$ and $V_{NTAT}$ to accomplish temperature compensation.

For example, an L-shape p-doped resistor with +4.4%/GPa can be employed in connection with the same or a different bandgap circuit with a current ratio of about 4.4/11 compared to the n-poly-based current. The L-shape of diffused resistors can make the stress coefficient independent to the direction of stress. The difference of the L-shaped arms can be used to separate X- and Y-stress dependencies of the reference.

The resulting resistor can then be designed to be nearly stress-compensated, or the ratio between both resistor types can be adjusted to compensate for remaining stress effects in comparator delay or reference voltages or capacitor. First order compensation of stress and temperature can be accomplished by adjustment based on a fixed ratio.

As explained above, different stress compensation signals can be generated for the X and Y directions to compensate for stress effects in a circuit bandgap or system reference. These stress effects correlate with the mechanical bending effects of the chip and are mainly responsible for lifetime shifts or package effects.

Figure 18:
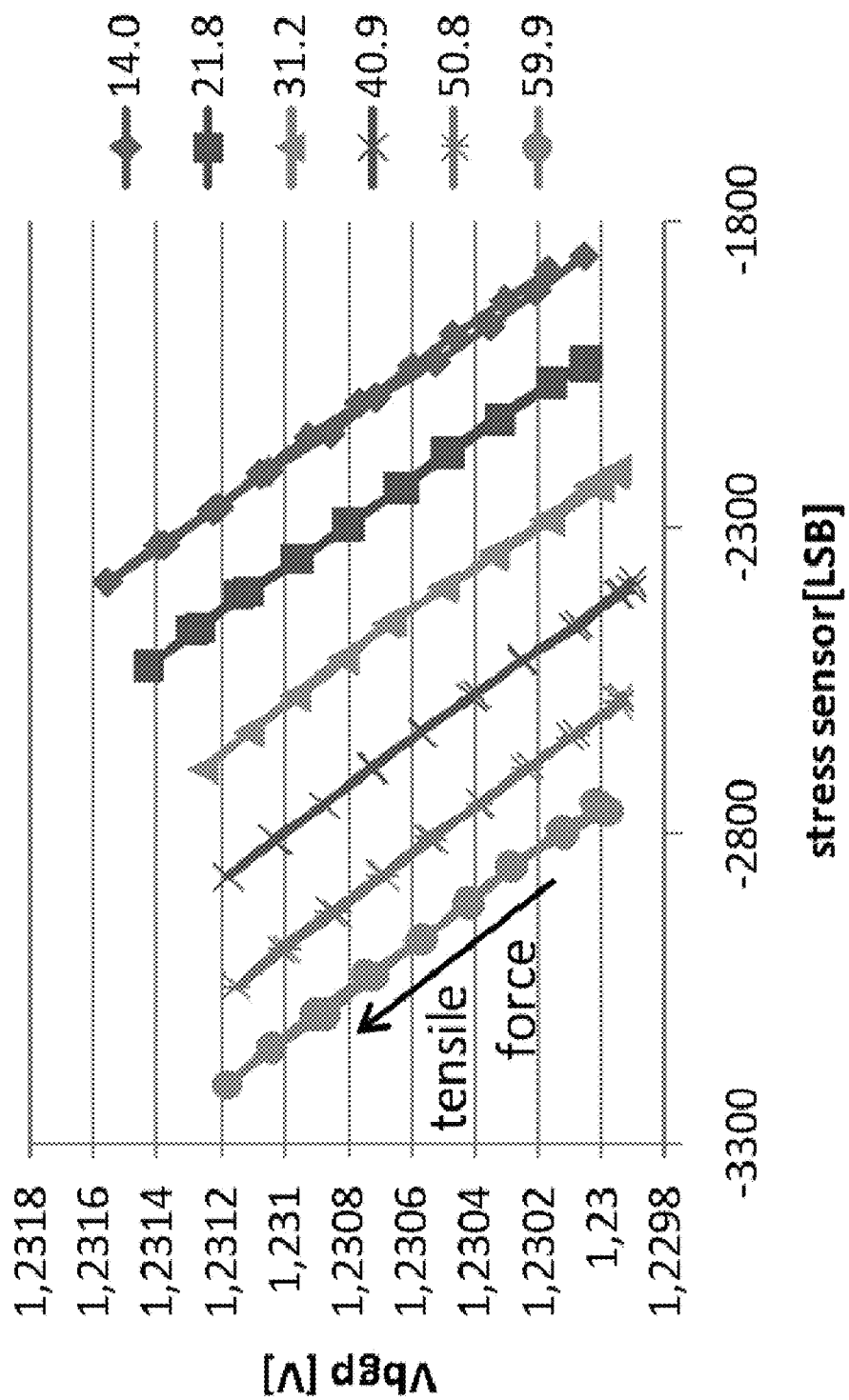
FIG. 18 is a graph illustrating correlation between stress sensor output and bandgap voltage.
Figure 19:
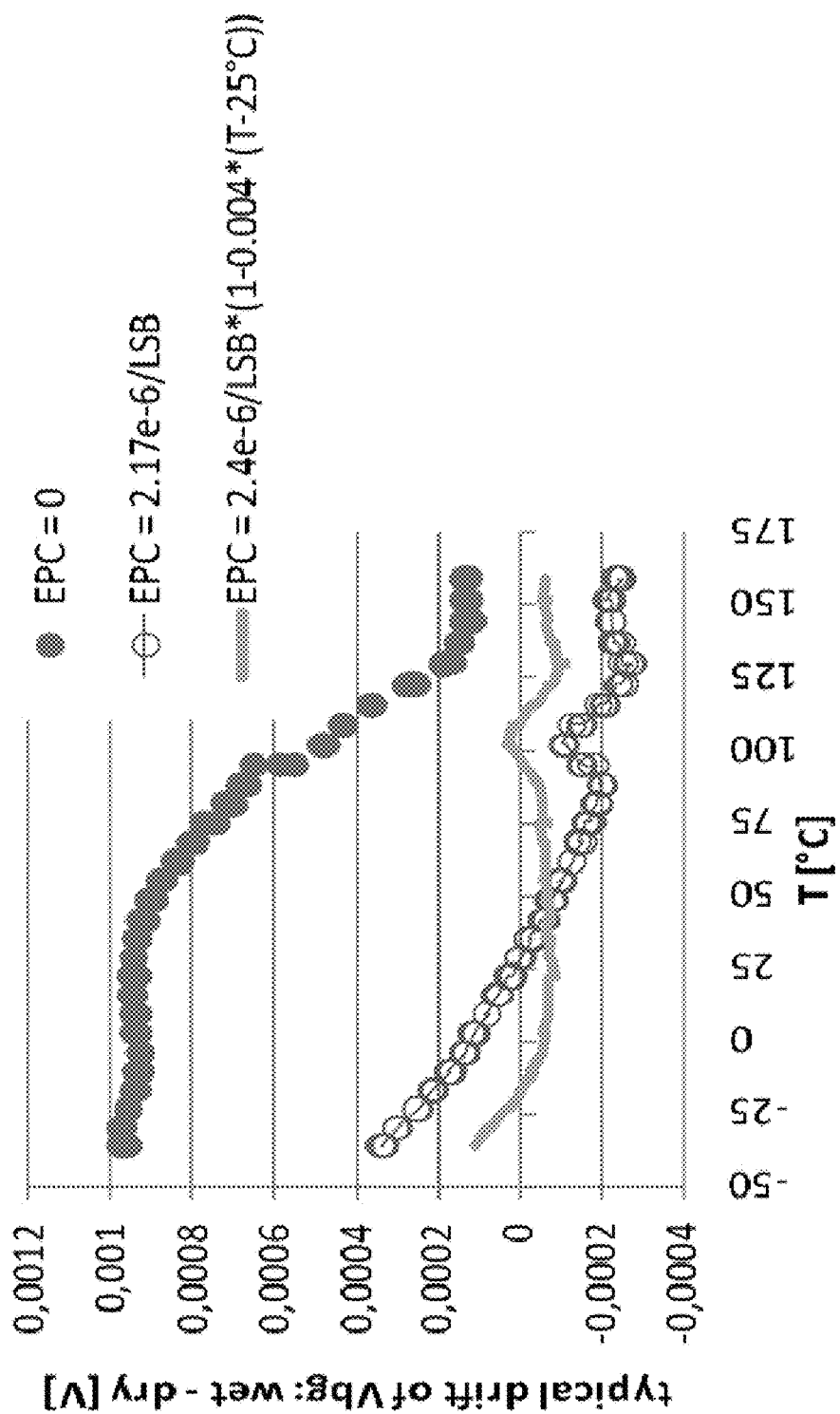
FIG. 19 is a graph illustrating bandgap voltage drift caused by humidity changes in plastic package without activated stress compensation and with activated stress compensation.

FIG. 18 illustrates a graph showing correlation between stress sensor output and bandgap voltage. FIG. 19 illustrates a graph showing bandgap voltage drift caused by humidity changes in plastic package without activated stress compensation and with activated stress compensation (shown as temperature independent compensation and temperature dependent compensation). As can be seen, with temperature dependent stress compensation, drift is significantly reduced.

In contrast to conventional systems and techniques, embodiments described herein can compensate for both local stress effects (e.g., within the reference circuit 110 and/or within the global stress compensation component 120) and global stress effects, whether mechanical or electrical in nature. Conventional stress compensation circuits can only compensate global in-plane mechanical stress effects, and only partially address electrical aging effects (e.g., different drift of $V_{th}$ over the lifetime of transistor pairs). However, local stress effects (e.g., in differential transistor pairs or in current mirrors for stress sensor(s), which can be caused by deep trenches in modern technologies) cannot be fully compensated by conventional systems, because of bad correlation of local stresses with global stress sensor signals, and because local stress effects are partially unpredictable. Additionally, electrical stress effects caused by bias voltage or bias current cause drift of threshold voltage of MOS transistors $V_{th}$ over their lifetimes.

In contrast, in aspects described herein, local stress effects (e.g., mechanical effects, electrical effects, aging effects, etc.) can be compensated by chopping and/or DEM. Moreover, if the reference circuit (e.g., bandgap reference, etc.) itself and the stress sensor(s) and associated ADC have local mismatch (e.g., caused by local stress effects) that is compensated by chopping and/or DEM, then the resulting accuracy has a multiplying effect, as discussed supra.

By combining compensation for both global and local stress effects, a number of consequences result that would not be possible with conventional systems. For example, even more predictable stress coefficients and correlations are realized, which has a significant impact on stress compensation, because systems will not have individualized stress compensation, thus the stability of this coefficient from sample to sample and for different production lots will impact the actual stress compensation in individual samples. Accordingly, by providing more stable coefficients, aspects described herein can improve the stability of references over the lifetime of individual samples. Additionally, embodiments discussed herein can employ quadratic or curvature compensation, while in conventional systems, the desired curvature compensation is destroyed with aging or packaging effects. In aspects described herein, electrical life-time drifts of stress sensitive circuits can be compensated by local stress components (e.g., DEM components, choppers, auto-zeroing components, etc.). Additionally, correlation from global to local stress effects can be used for compensation, when local mismatch is excluded (e.g., by chopping or DEM). In aspects, stress effects can be compensated even when the effects of stress are significantly different in different directions (e.g., a resistor to and near a trench, or perpendicular to and near a trench). Because of the nature of compensation for stress effects as discussed herein, a bandgap could be trimmed on wafer even before packaging, because packaging effects are effectively eliminated by compensation. Additionally, in aspects employing an ADC, the clock of the ADC can be divided and used in a synchronous way for any chopping, auto-zeroing or DEM of local stress compensation components.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations. In addition, while a particular feature may have been disclosed with respect to only one of several implementations, such feature may be combined with one or more other features of the other implementations as may be desired and advantageous for any given or particular application.

What is claimed is:

1. A method, comprising:
   generating at least one reference signal via a reference circuit, wherein generating the reference voltage comprises compensating, via the reference circuit, for stress effects shown via the at least one reference signal, wherein the at least one reference signal comprises at least one of a reference voltage, a reference current, or a reference clock frequency;
   sensing at least one stress component of a system comprising the reference circuit via at least one stress sensor, wherein each stress component of the at least one stress component of the system is one of a component of a stress tensor of the system or a linear combination of components of the stress tensor of the system; and
   compensating for the stress effects shown via the at least one reference signal based on the sensed at least one stress component.

2. The method of claim 1, wherein compensating, via the reference circuit, for the stress effects shown via the at least one reference signal comprises employing dynamic element matching (DEM) to cycle between at least one of a plurality of transistors of the reference circuit or a plurality of resistors of the reference circuit.

3. The method of claim 1, wherein compensating, via the reference circuit, for the stress effects shown via the at least one reference signal comprises chopping or auto-zeroing at least one of an input signal of an amplifier of the reference circuit or an output signal of the amplifier of the reference circuit.

4. The method of claim 1, wherein sensing at least one stress component comprises sensing at least two distinct stress components, and wherein compensating for the stress effects shown via the at least one reference signal based on the sensed at least one stress component comprises compensating for the stress effects shown via the at least one reference signal based on the sensed at least two distinct stress components.

5. The method of claim 1, wherein the at least one stress sensor comprises a plurality of stress sensors, and further comprising employing dynamic element matching (DEM) to cycle between the plurality of stress sensors to compensate for stress effects on the plurality of stress sensors.

6. The method of claim 1, wherein the reference circuit comprises at least one of an amplifier or an analog-to-digital converter (ADC), and the sensing is performed using an auto-zeroing component or a chopper, further comprising eliminating an offset of an input signal or an output signal of the amplifier or the ADC using the auto-zeroing component or the chopper.

7. The method of claim 1, wherein the at least one stress sensor comprises a plurality of stress sensors, and wherein sensing at least one stress component comprises sensing a plurality of distinct stress components, respectively.

8. The method of claim 1, wherein the at least one stress sensor comprises a temperature sensor configured to sense at least one temperature, and wherein compensating for the stress effects comprises compensating for temperature effects shown via the at least one reference signal based at least in part on the sensed at least one temperature.

9. The method of claim 1, wherein compensating is performed with a stress compensation component that comprises a sensor analog-to-digital converter (ADC) that measures the at least one stress component based on the sensed at least one stress component.

10. The method of claim 9, wherein compensating is further performed with a set of local stress compensation components, wherein the set of local stress compensation components comprises at least one of an sensor ADC auto-zeroing component or a sensor ADC chopper, wherein the sensor ADC auto-zeroing component or the sensor ADC chopper is configured to eliminate an offset of an input signal or an output signal of the sensor ADC.

11. The method of claim 9, wherein compensating is further performed with a compensation digital-to-analog converter (DAC) configured to receive an output signal from the sensor ADC, and configured to generate a compensation output signal, and is further configured to compensate for the stress effects on the at least one reference signal based at least in part on adjusting the reference voltage based on the compensation output signal.

* * * * *